(12) United States Patent
Leblanc et al.

(10) Patent No.: US 12,264,964 B2
(45) Date of Patent: Apr. 1, 2025

(54) SYSTEM AND DEVICES FOR MEASURING LIGHT SOURCES AND METHODS OF USE THEREOF

(71) Applicant: BlueLight Analytics, Inc., Halifax (CA)

(72) Inventors: Derek Leblanc, St. John's (CA); Chris Felix, Beaver Bank (CA)

(73) Assignee: BlueLight Analytics, Inc., Halifax (CA)

( * ) Notice: Subject to any disclaimer, the term of this patent is extended or adjusted under 35 U.S.C. 154(b) by 792 days.

(21) Appl. No.: 17/286,715

(22) PCT Filed: Oct. 21, 2019

(86) PCT No.: PCT/CA2019/051490
§ 371 (c)(1),
(2) Date: Apr. 19, 2021

(87) PCT Pub. No.: WO2020/077468
PCT Pub. Date: Apr. 23, 2020

(65) Prior Publication Data
US 2021/0389175 A1    Dec. 16, 2021

Related U.S. Application Data

(60) Provisional application No. 62/867,442, filed on Jun. 27, 2019, provisional application No. 62/790,138, (Continued)

(51) Int. Cl.
*G01J 1/04*    (2006.01)
*A61C 13/15*   (2006.01)
(Continued)

(52) U.S. Cl.
CPC ........... *G01J 1/0422* (2013.01); *A61C 19/003* (2013.01); *G01J 1/0474* (2013.01); *G06N 3/084* (2013.01);
(Continued)

(58) Field of Classification Search
CPC .............. G01J 1/0422; G01J 1/0474; G01J 2001/4247; G01J 2001/446; H04W 4/38; H04W 4/80; A61C 19/003; G06N 3/084
See application file for complete search history.

(56) References Cited

U.S. PATENT DOCUMENTS

| 4,445,858 A | 5/1984 | Johnson |
| 5,471,053 A | 11/1995 | Diner et al. |

(Continued)

FOREIGN PATENT DOCUMENTS

| CN | 104797912 A | 7/2015 |
| DE | 2417399 A1 | 10/1975 |

(Continued)

OTHER PUBLICATIONS

Extended European Search Report for European Patent Application No. 19872759.6, dated Sep. 27, 2022 (10 pages).
(Continued)

*Primary Examiner* — Anne M Hines
(74) *Attorney, Agent, or Firm* — Clark & Elbing LLP

(57) ABSTRACT

The invention provides a system and related equipment for the precise measurement of the output characteristic of a light source, e.g., a dental light curing unit (LCU) or light for photodynamic therapy, using a light collector, a light detector, and a computer programmed to deliver the value of the output characteristic of the light source to the user. The systems allow for the determination of a proper 5 exposure time or the selection of a light source as needed for a specific application. The invention also provides a light device.

10 Claims, 18 Drawing Sheets

Related U.S. Application Data filed on Jan. 9, 2019, provisional application No. 62/747,969, filed on Oct. 19, 2018.

(51) Int. Cl.
| | |
|---|---|
| *G06N 3/084* | (2023.01) |
| *H04W 4/38* | (2018.01) |
| *H04W 4/80* | (2018.01) |
| *G01J 1/42* | (2006.01) |
| *G01J 1/44* | (2006.01) |

(52) U.S. Cl.
CPC .............. *H04W 4/38* (2018.02); *H04W 4/80* (2018.02); *G01J 2001/4247* (2013.01); *G01J 2001/446* (2013.01)

(56) References Cited

U.S. PATENT DOCUMENTS

| | | | |
|---|---|---|---|
| 6,437,861 | B1 | 8/2002 | Kuta |
| 6,485,301 | B1 | 11/2002 | Gemunder et al. |
| 7,729,941 | B2 | 6/2010 | Zampini, II et al. |
| 9,310,298 | B2 | 4/2016 | Labrie et al. |
| 9,693,845 | B2 | 7/2017 | Price |
| 10,113,906 | B2 | 10/2018 | Labrie et al. |
| 10,816,394 | B2 | 10/2020 | Labrie et al. |
| 2002/0187454 | A1* | 12/2002 | Melikechi ............ A61C 19/004 433/29 |
| 2002/0187455 | A1* | 12/2002 | Melikechi ............ A61C 19/004 433/29 |
| 2004/0101312 | A1 | 5/2004 | Cabrera |
| 2005/0200311 | A1 | 9/2005 | Youle |
| 2007/0036467 | A1 | 2/2007 | Coleman et al. |
| 2007/0037113 | A1 | 2/2007 | Scott et al. |
| 2008/0023625 | A1 | 1/2008 | Plank et al. |
| 2008/0062413 | A1 | 3/2008 | Ashdown et al. |
| 2009/0114844 | A1 | 5/2009 | Plank et al. |
| 2010/0140450 | A1 | 6/2010 | Duret et al. |
| 2011/0108741 | A1 | 5/2011 | Ingram |
| 2012/0019819 | A1 | 1/2012 | Messerchmidt |
| 2012/0266740 | A1 | 10/2012 | Hilbish et al. |
| 2017/0035539 | A1 | 2/2017 | Bringley |
| 2019/0336259 | A1 | 11/2019 | Elmore et al. |
| 2020/0375711 | A1 | 12/2020 | Leblanc et al. |

FOREIGN PATENT DOCUMENTS

| | | |
|---|---|---|
| JP | H05-280960 A | 10/1993 |
| JP | H11-137574 A | 5/1999 |
| JP | 2002-296115 A | 10/2002 |
| JP | 2008-32728 A | 2/2008 |
| JP | 2009-115797 A | 5/2009 |
| JP | 2011-220770 A | 11/2011 |
| JP | 2015-161683 A | 9/2015 |
| JP | 2015-530573 A | 10/2015 |
| WO | WO-2004/079314 A1 | 9/2004 |
| WO | WO-2014/036660 A1 | 3/2014 |
| WO | WO-2016/075639 A1 | 5/2016 |
| WO | WO-2019/036817 A1 | 2/2019 |

OTHER PUBLICATIONS

International Search Report and Written Opinion for International Patent Application No. PCT/CA2019/051490, mailed Jan. 2, 2020 (13 pages).

* cited by examiner

Input of lights' spectral profile and raw photodiode normalized voltage

SYSTEM AND DEVICES FOR MEASURING LIGHT SOURCES AND METHODS OF USE THEREOF

BACKGROUND OF THE INVENTION

Dental restorations often involve a light-curable resin that is hardened to a cure strength by exposure to light in the visible and/or ultraviolet (UV) spectrum. While dental resin restorations represent a significant market, over 60% of all restorative dentistry is for the replacement of existing restorations. Placement of resin restorations is technique-sensitive, and such restorations must be placed properly to deliver the best health care to patients. The most common cause of failure of resin restorations is secondary caries (tooth decay) due to micro-leakage around the restoration, followed by restoration fracture, and marginal defects. These failures may be due to the fact that the resin restoration was inadequately polymerized and did not reach its intended physical properties.

Inadequately cured resins may result in reduced physical properties of the restoration, reduced bond strengths, increased wear and breakdown at the margins of the restoration, decreased biocompatibility, and increased DNA damage from leachates, such as bisphenol A diglycidylether methacrylate (Bis-OMA), tetraethyleneglycol dimethacrylate (TEGDMA), 1,6-bis(methacryloxy-2-ethoxycarbonylamino)-2,4,4-trimethylhexane (UDM), and 2,2-bis(4-(2-Methacryloxyethoxy)phenylpropane (bis-EMA). Conversely, too much curing energy delivered to the restoration may cause an unnecessary and unacceptable temperature increase in the tooth and surrounding oral tissues.

Typical instruments for measuring the output power of light sources are not portable and/or have high operating costs. There is a need in the art to develop a portable system that can quickly collect and measure light from an external source and relay the information in real time, e.g., to enable a clinician to make adjustments to curing times.

SUMMARY OF THE INVENTION

We have developed a system and related equipment for the precise measurement of an output characteristic, e.g., the output power, of a light source, e.g., a dental light curing unit (LCU) or light for photodynamic therapy, using a light collector, a light detector, and a computer programmed to deliver an output characteristic, e.g., the output power, of the light source to the user. The system allows, for example, for the determination of a proper exposure time or the selection of a light source as needed for a specific application.

In one aspect, the invention provides a light collection device having a light collector that includes a spacer having a top aperture and a bottom aperture. The device includes a light diffusing layer positioned to diffuse light passing through at least a portion of the top aperture. The device may further include a non-spectral light detector configured to produce a signal from light entering the device, in particular a photovoltaic detector. In some embodiments, the non-spectral light detector is connected to the bottom aperture of the spacer, e.g., a recess in the bottom aperture.

The spacer may be enclosed in an external shell having an entrance for light to enter the device. The external shell may include a solid material, e.g., plastic, ceramic, glass, or metal (e.g., brass). In some cases, the device may further include additional components, such as a screen and/or a filter, e.g., a filter above or below the screen. The screen and/or filter is positioned adjacent to the entrance for light to enter the device and/or the top aperture. In some embodiments, the screen may be substantially square, circular, or disc-shaped and may be sized to cover the top aperture of the spacer. In any of the above embodiments, the filter may be selected from a group consisting of glass, a neutral density filter, a band pass filter, and a blue band pass filter. In any of the above embodiments, the filter may filter wavelengths greater than 500 nm (e.g., 510 nm, 550 nm, 600 nm, 700 nm, or 800 nm). The filter may also physically protect the screen from damage, i.e., be located on top of or external to the screen.

In any of the above embodiments, the light diffusing layer allows for substantially uniform light diffusion. The spacer includes, e.g., polytetrafluoroethylene (e.g., Teflon® or Spectralon® from Labsphere Inc.), polyoxymethylene (e.g., Delrin®), barium sulfate (e.g., 6080 White Reflectance Coating from Labsphere Inc.), polyvinylchloride, polyamide, e.g., Nylon, co-polyester, poly-lactic acid (PLA), or a Lambertian coating (e.g., Spectraflect® or Duraflect® from Labsphere Inc.), in particular, co-polyester.

In particular embodiments, the entrance of the external shell includes a resting location, e.g., to rest a light source in a stable, repeatable position. The resting location may be configured to align the central axis of the light source with the center of the spacer or light detector. In particular embodiments, the entrance is irregularly shaped, e.g., tear drop shaped or other shape to position the light source in a desired location, e.g., aligned with the center of the light detector. In further embodiments, the device, e.g., at or adjacent to the entrance, e.g., at or adjacent a resting location, includes a sensor and/or an actuator. The sensor may be a proximity, motion, or force, e.g., applied force, sensor, and the actuator may be a mechanical actuator, such as a button that is depressed when the light source is in position. The sensor or actuator may be used to signal when the light source is in the correct position. This signal can be used to initiate data collection or to inform the user that the device is ready to obtain data.

In another aspect, the invention features a system for the determination of an output characteristic, e.g., the output power, of a light source, the system having a light collecting device; a non-spectral light detector configured to produce a signal from light collected by the light collector; and a computer programmed to provide an output characteristic, e.g., the output power, of the light source from the signal produced by the light detector. In some embodiments, the light collecting device is the device described herein. In one embodiment, the computer is programmed with a neural network. In certain embodiments, the neural network is trained with the spectral profiles of a plurality of light sources including the light source. In further embodiments, the neural network is trained with a plurality of input values for an optical characteristic, e.g., the responsivity curve, of the light detector. In some embodiments, the input data for the neural network is a function of the optical characteristic, e.g., responsivity curve, of the light detector. In some embodiments, the input data for the neural network is normalized to values between 0-1. In further embodiments, the system has a mobile device that communicates with the computer to provide, e.g., display, the output characteristic, e.g., the output power, of the light source. In one embodiment, the mobile device is a handheld device. In one embodiment, the light detector is a photodiode, a photomultiplier tube, a CCD array, a CMOS sensor, or a photovoltaic device. In some embodiments, the computer communicates wirelessly to the light detector.

Another aspect of the invention features a computer programmed with a neural network whose input data is a function of a signal produced by a light detector to determine an output characteristic, e.g., the output power, of a light source. The neural network has a plurality of input nodes. Each input node is configured to contain at least one data point; a plurality of hidden nodes grouped in a plurality of layers, wherein each of the plurality of hidden nodes receives as input all of the at least one data points from the plurality of input nodes; and an output node, wherein the plurality of hidden nodes and output node are trained with the spectral profiles of a plurality of light sources including the light source being measured. In some embodiments, the hidden nodes and output node are further trained with an optical characteristic, e.g., the responsivity curve, of the light detector. In some embodiments, the data on each of the plurality of hidden nodes is summed before being passed to the plurality of hidden nodes in the next layer. In some embodiments, the data passed between hidden nodes is statistically weighted using the spectral profiles of a plurality of light sources including the light source and the optical characteristic, e.g., responsivity curve, of the light detector. In further embodiments, the plurality of hidden nodes contains a transfer function to update the statistical weights of each of the plurality of hidden nodes. In some embodiments, the derivative of the transfer function is used to update the statistical weights of each of the plurality of hidden nodes. In one embodiment, the transfer function is a sigmoidal. In other embodiments, the transfer function is a rectified function or a combination of sigmoidal and rectified, e.g., in different layers. In some embodiments, the data from the plurality of hidden nodes in the last of the plurality of layers are passed to the output node. In further embodiments, the output node contains a sigmoid transfer function. In some embodiments, wherein the output node returns a value representative of an output characteristic, e.g., the output power, of the light source.

In another aspect, the invention features a system for the determination of an output characteristic, e.g., the output power, of a light source, the system having a light collecting device; a light detector configured to produce a signal from light collected by the light collector; and a computer programmed with a neural network to provide an output characteristic, e.g., the output power, of the light source from input data corresponding to the signal produced by the light detector. In some embodiments, the light collecting device is the device described herein. In certain embodiments, the neural network is trained with the spectral profiles of a plurality of light sources including the light source. In further embodiments, the neural network is trained with a plurality of input values for an optical characteristic, e.g., the responsivity curve, of the light detector. In some embodiments, the input data for the neural network is a function of the optical characteristic, e.g., responsivity curve, of the light detector. In some embodiments, the input data for the neural network is normalized to values between 0-1. In further embodiments, the system has a mobile device that communicates with the computer to provide, e.g., display, an output characteristic, e.g., the output power, of the light source. In one embodiment, the mobile device is a handheld device. In some embodiments, the computer communicates wirelessly to the light detector.

In a related aspect, the invention provides a method of determining an output characteristic, e.g., the output power, of a light source by collecting light from a light source with a light collecting device and light detector to produce a signal; sending the signal to a computer programmed with a neural network, as described herein, to determine an output characteristic, e.g., the output power of the light source; and providing, e.g., displaying, an output characteristic, e.g., the output power, to the user. In some embodiments, the light collecting device is the device described herein. In some embodiments, the computer communicates wirelessly to the light detector. In some embodiments, the computer communicates wirelessly with a mobile device. In one embodiment, the mobile device is a handheld device.

In another related aspect, the invention provides a method of determining an output characteristic, e.g., the output power, of a light source by collecting light from a light source with a light collecting device and non-spectral light detector to produce a signal; sending the signal to a computer programmed with a neural network to determine an output characteristic, e.g., the output power, of the light source; and providing, e.g., displaying, an output characteristic, e.g., the output power, to the user. In some embodiments, the light collecting device is the device described herein. In one embodiment, the signal produced from the non-spectral light detector is a voltage. In some embodiments, the computer communicates wirelessly to the non-spectral light detector. In some embodiments, the computer communicates wirelessly with the mobile device. In one embodiment, the mobile device is a handheld device.

In another aspect, the invention provides a method of determining an output characteristic of a light source by receiving a signal from light collected from a light source with a light collecting device and non-spectral light detector; and using the signal in a computer programmed to determine the output characteristic of the light source. In a related aspect, the invention provides a method of determining an output characteristic of a light source by receiving a signal from light collected from a light source with a light collecting device and light detector; and using the signal in a computer programmed with a neural network, as described herein, to determine the output characteristic of the light source. These methods may further include providing the output characteristic to a user. In any of these embodiments, the light collecting device is the device described herein.

In a further aspect, the invention provides a non-transitory computer memory programmed to carry out the determination of an output characteristic of a light source as described herein.

In any aspect of the invention, the output characteristic may be output power, output energy, output flux, a calculated spectrum, irradiance, calculated light source age, or calculated exposure time.

The invention further provides a device including a light diffusing element including a top portion having a screen allowing the passage of light; a bottom portion having an inner surface that is substantially hemispherical, and a side portion having an inner surface that is substantially cylindrical and an outlet port. The side portion is connected to the top portion and the bottom, and the outlet port is separated from the inner surface by a diffusive material, which may or may not be the same material as that of the inner surface.

The device may further include a filter above or below the screen. In certain embodiments, the device further includes a light detector, e.g., a non-spectral light detector, configured to produce a signal from the light in the outlet port. In other embodiments, the light diffusing element prevents light from penetrating through the side portion or the bottom portion except via the outlet port. The light diffusing element may allow for substantially uniform light diffusion across the inner surfaces. The inner surfaces and/or screen include, for example, polytetrafluoroethylene, barium sulfate, or polyoxymethylene. The screen may also include a transparent or translucent material and/or be coated with a translucent Lambertian coating.

In certain embodiments, the height of the substantially cylindrical inner surface of the side portion is between 1 mm and 50 mm, e.g., between 1 mm and 15 mm. In other embodiments, the top further includes an aperture. The aperture in the top portion of the light diffusing element may have a diameter between 1 mm and 300 mm, e.g., between 4 mm and 30 mm. In yet other embodiments, the outlet port has a diameter between 1 and 20 mm, e.g., between 5 and 15 mm. In further embodiments, the diameter of the substantially cylindrical inner surface of the side portion and/or the substantially hemispherical inner surface of the bottom portion is between 1 and 30 mm, e.g., between 15 and 25 mm.

The invention further provides a device including a light diffusing element including a top portion having a screen allowing the passage of light; a bottom portion having an inner surface that is substantially hemispherical, and a side portion having an inner surface that is substantially cylindrical and an outlet port. The side portion is connected to the top portion and the bottom, and the outlet port is separated from the inner surface by a diffusive material, which may or may not be the same material as that of the inner surface.

We have also developed a device, i.e., curing light or photodynamic therapy light, and related system that delivers the appropriate amount of energy, e.g., to cure a dental resin or photodynamically treat a patient. The device includes a light source and a controller that is operably connected to the light source to control a length of time that the light source emits light. The controller is in data communication with an external computer programmed to determine the length of time, which may be continuous or in multiple cycles. The controller may also be in data communication with the external computer to determine the output power of the light source.

In one aspect, the invention provides a device including a) a light source emitting light and b) a controller operatively coupled to the light source to control a length of time that the light source emits light externally from the device. The controller is in data communication with an external computer. The external computer may be programmed to determine the length of time and transmit the length of time to the controller. Alternatively, the controller may be programmed to calculate the length of time from data received from the external computer.

In embodiments, the device further includes a battery to provide power to the light source or a power cord to provide power to the light source. In further embodiments, the data communication is wireless. The computer may determine the length of time from a measurement of an output characteristic, e.g., output power, of the light source. In certain embodiments, the length of time is sufficient to cure the dental resin in a tooth cavity. Alternatively, the length of time is sufficient to treat a patient photodynamically.

In certain embodiments, the light source includes an LED, e.g., a plurality of LEDs that emit different spectra. In certain embodiments, the light emitted is between 100 and 2500 nm. In certain embodiments, the light emitted is suitable to polymerize a dental resin. In certain embodiments, the device further includes a tip from which light is emitted, e.g., where the tip is sized to fit into the mouth of an adult human.

In one aspect, the invention provides a system including a light device as described herein and the external computer. In certain embodiments, the system further includes a light detector in data communication with the external computer and/or a light collector. The light detector may be non-spectral. In certain embodiments, the system further includes a mobile device that communicates with the light detector and external computer to provide an output characteristic of the light source. In certain embodiments, the external computer or controller is further programmed to determine the output power of the device over the length of time.

In one aspect, the invention provides a method of polymerizing a dental resin by providing a device as described herein; providing an output characteristic of the device to an external computer, wherein the controller is in data communication with an external computer to determine a length of time of light emission based on the output characteristic; and positioning the device adjacent the resin, wherein the device emits light for the length of time, thereby polymerizing the resin. The method may further include the external computer determining the output power of the device over the length of time or communicating data to the controller to determine the output power of the device over the length of time. In certain embodiments, the length of time is divided over two or more on/off cycles. The external computer may determine the length of time of light emission based on the output characteristic or communicate data to the controller to determine the length of time of light emission based on the output characteristic.

In one aspect, the invention provides a method of photodynamically treating a patient by providing a device as described herein; providing an output characteristic of the device to an external computer, wherein the controller is in data communication with an external computer to determine a length of time of light emission based on the output characteristic; positioning the device adjacent the patient, wherein the device emits light for the length of time, thereby photodynamically treating the patient. The method may further include the external computer determining the output power of the device over the length of time or communicating data to the controller to determine the output power of the device over the length of time. In certain embodiments, the length of time is divided over two or more on/off cycles. The external computer may determine the length of time of light emission based on the output characteristic or communicate data to the controller to determine the length of time of light emission based on the output characteristic.

BRIEF DESCRIPTION OF THE DRAWINGS

FIG. 3A is a bottom view of the spacer with the recess for a light detector. FIGS. 3B and 3C are side views of the spacer showing a circular top aperture. FIG. 3D is a bottom view of the spacer with the recess for a light detector. FIG. 3E is a side view of the spacer. FIG. 3F is a top view of the spacer looking down the vertical axis from the top aperture to the bottom aperture.

FIG. 4A is a bottom view of the top portion of the external shell with the recess for the spacer and the entrance. FIG. 4B is a top view of the bottom portion of the external shell with recesses for a power supply and microcontroller. FIG. 4C is a bottom view of the top portion of the external shell indicating placement of the spacer in the top portion of the external shell.

FIG. 5A is an exterior view of the device showing the location of the entrance to the shell. FIG. 5B is bottom view of the device showing the cylindrical shape of the spacer with a recess for a light detector.

FIG. 6A is a front view of the external shell showing the resting location. FIG. 6B is a side view of the device. FIG. 6C is a top view of the device. FIG. 6D is a perspective view of the device.

FIG. 6A is a graph of power data measured with a photodiode-based neural network system, and FIG. 6B is a graph of power data measured with a spectrometer.

DETAILED DESCRIPTION OF THE INVENTION

The present invention provides devices and systems for determining an output characteristic, e.g., output power, of a light source, e.g., a light curing unit (LCU) used in dental restorations or a light used in photodynamic therapy. The devices, systems, and methods may be generally employed with any light source, including incandescent, laser, LED, halogen, fluorescent, plasma arc, or solar. Information from the invention can be used to calculate exactly how much light is needed for a given process or procedure, e.g., to cure a photosensitive resin material without overexposure. An advantage of the system is that it allows the end user to determine an output characteristic, e.g., power, without obtaining spectral data.

Figure 1:
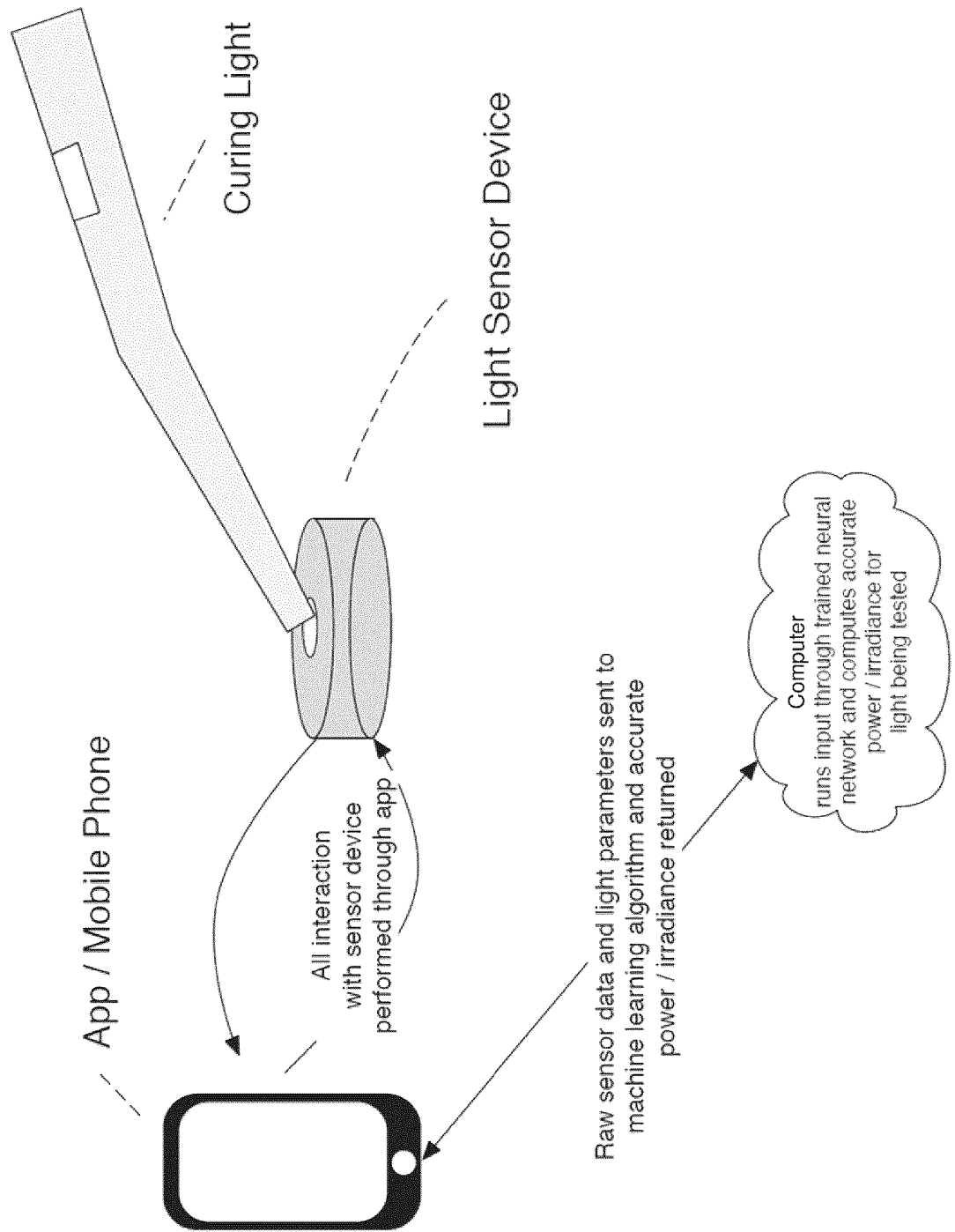
FIG. 1: Scheme describing how a system of the invention may be used to measure an output characteristic, e.g., the output power, of a dental light curing unit (LCU) and provide, e.g., display, the result to the user.

In one aspect, the system includes a light collector for the light emitted from the light source, a light detector configured to produce a signal from the light collected by the light collector, and a computer programmed to provide the output characteristic, e.g., power, of the light source from the signal produced by the light detector. In particular, the system does not require the use of a spectral detector to produce an output characteristic, e.g., the output power, of a light source, i.e., the light detector is not required to measure intensity as function of wavelength. Typically, the light source will produce light in the range of the IR to UV, e.g., between 100 and 2500 nm, e.g., between 190 and 1100 nm. The light detected may be a subset of the spectrum produced by the light source. For example, various filters may be employed on the light source, the light collector, or separately to control the spectrum detected. In certain embodiments, the light detected is in the visible range, e.g., between 360 and 540 nm. An advantage of the system is that the light collector may communicate remotely, e.g., wirelessly, with the computer, allowing the measurement of an output characteristic, e.g., the output power, to be performed in most locations. This feature is advantageous as the light source may not be portable or easily moved to the location of the computer. A scheme describing how a system of the invention may be used to measure an output characteristic, e.g., the output power, of a light source, e.g., a dental light curing unit (LCU), and provide, e.g., display, the result to the user is shown in FIG. 1.

This system may be implemented in one or more parts. For example, each of the light collector, light detector, and computer may be a separate component, or two or more of the components may be physically connected. When separate components are employed, the computer, or a part of it, may be in a physically different location than the light collector and/or light detector. Furthermore, the light detector may interface with or be a part of a mobile device, e.g., cellular telephone or other handheld device, that can communicate with the computer, e.g., wirelessly. Functions of the computer may also be distributed over several processors or cores, which may or may not be physically linked.

In another aspect, the invention provides a light device including a light source and a controller operably connected to the light source to control a length of time that the light source emits light.

Devices

Light Collectors

Any suitable light collector may be employed in the invention. A preferred light collector is one that allows for the collection of light that is not dependent on the angle that light enters the collector, e.g., as described in WO 2014/036660, hereby incorporated by reference. Another light collector is described in WO 2019/036817, hereby incorporated by reference. Schematics of light collectors useful for the invention are shown in FIGS. 2A-2B and FIGS. 3A-3F.

Figure 2A:
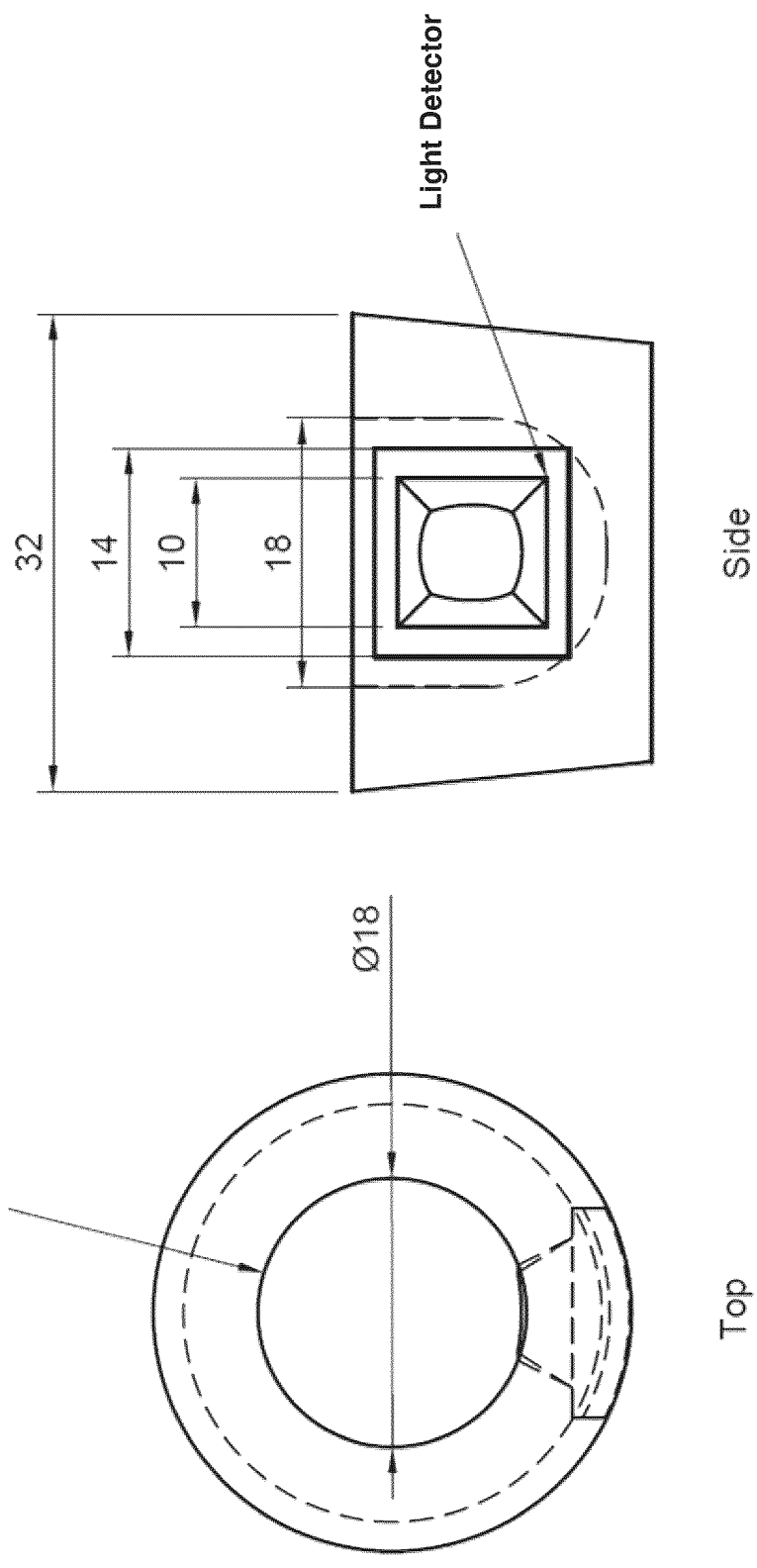
FIGS. 2A-2B: Technical drawings of light collectors showing the locations of the entrance to the collector and light detector. Dimensions are in mm.
Figure 2B:
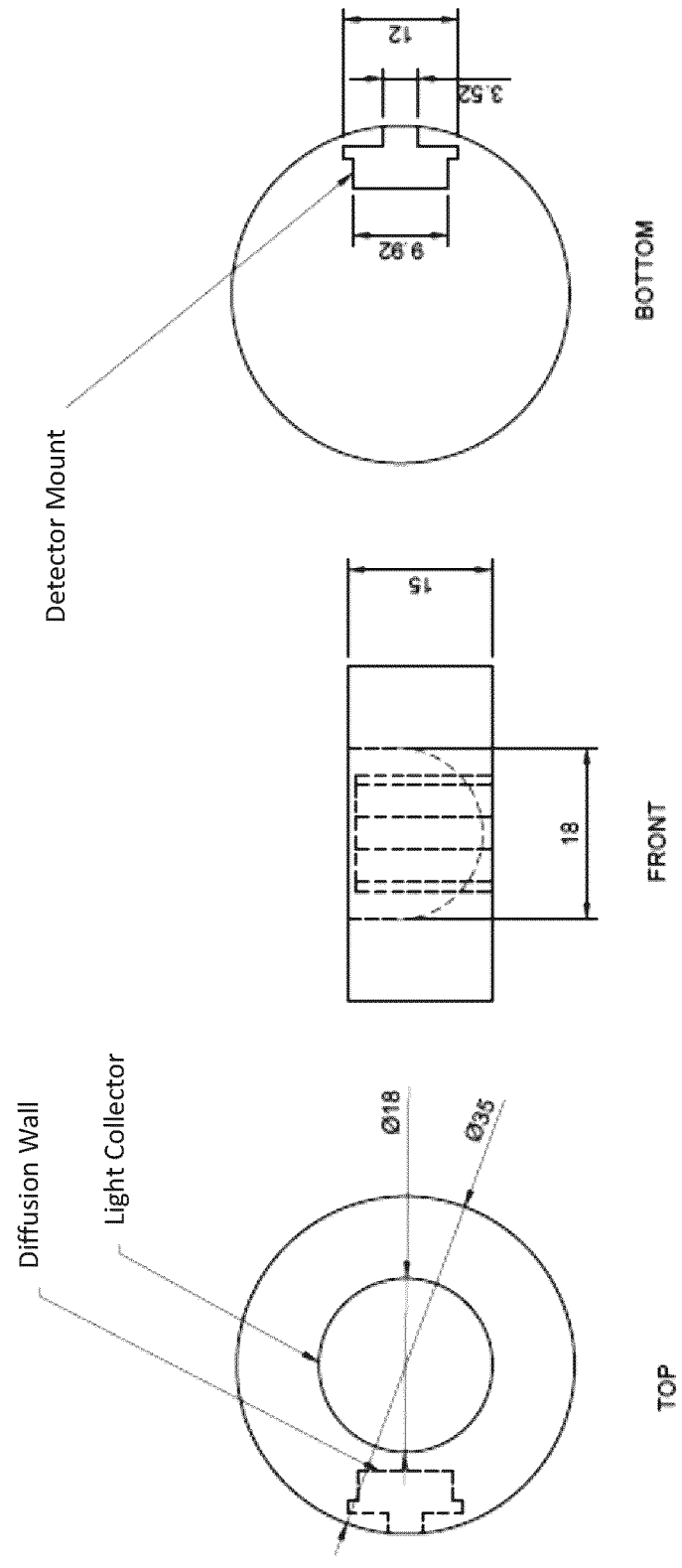

An exemplary light collector to be used with the invention contains a light diffusing element that includes top portion that includes a screen and an optional aperture, a bottom portion that includes an inner surface that is substantially hemispherical, and a side portion that includes an inner surface that is substantially cylindrical. The side portion further includes an outlet port. The light diffusing element may or may not be enclosed within an external shell. The side, bottom, and top portions may be manufactured from any suitable material, e.g., polytetrafluoroethylene (e.g., Teflon® or SpectraIon® from Labsphere Inc.), polyoxymethylene (e.g., Delrin®), barium sulfate (e.g., 6080 White Reflectance Coating from Labsphere Inc.), polyvinylchloride (PVC), polyamide, e.g., Nylon, co-polyester, poly-lactic acid (PLA), or a Lambertian coating (e.g., Spectraflect® or Duraflect® from Labsphere Inc.). These portions may also include other materials, e.g., plastic, ceramic, glass, or metal, on which Lambertian materials are layered or coated. When the top portion includes an aperture, the portions of the top not including the screen may be made from any material suitable to hold the screen, e.g., plastic, ceramic, glass, or metal. The surface of a screen, e.g., the material of the surface or a coating applied to the surface, is white, translucent, and Lambertian, e.g., made from or coated with polytetrafluoroethylene (e.g., Teflon® or Spectralon® from Labsphere Inc.), polyoxymethylene (e.g., Delrin®), barium sulfate (e.g., 6080 White Reflectance Coating from Labsphere Inc.), polyvinylchloride (PVC), polyamide, e.g., Nylon, co-polyester, poly-lactic acid (PLA), or a Lambertian coating (e.g., Spectraflect® or Duraflect® from Labsphere Inc.). The screen is located above the side and bottom portions of light diffusing element of the light collector. When the top includes an aperture, the screen may be sized to cover at least the aperture of light diffusing element. The length of the screen may be equal to or greater than the diameter of the substantially hemispherical bottom portion. In some embodiments, the device may include a filter, e.g., glass (such as alkali-aluminosilicate sheet toughened glass (Gorilla® glass)), neutral density filter, blue band filter, or a filter that filters wavelengths of at least 500 nm. The filter may be located in the top portion of light diffusing element above or below the screen. In certain embodiments, the filter acts as a physical barrier to protect the screen from damage. When an aperture is present in the top portion, it may include one or more tiered recesses into which the screen and any filter rest. The tiered recesses provide physical support for the perimeter of the screen and filter. Alternative ways of attaching a screen and/or filter are known in the art. For example, the screen may be part of a component that screws or clamps to the side and bottom portions. The screen may also be a sheet of material that is compressed against the side portion, e.g., by the external housing. The exterior shape of optional external shell may be substantially cubical, cylindrical, pyramidal, or a rectangular solid. The internal surface and cavity shape of external shell may vary according to the external shape of the light diffusing element, e.g., it may conform to the exterior shape. In certain embodiments, as shown in FIG. 2A, the outlet port includes an opening from the inner surface of the side portion. In other embodiments, as shown in FIG. 2B, the outlet port is separated from the inner surface by a diffusive material. The diffusive material may be the material of the inner surface or a different material, e.g., placed in an opening in the inner surface. It will be apparent that the diffusive material allows the passage of light from the inner surface to the outlet port.

In some cases, a light collecting device, e.g., to be used as part of the system of the invention, contains a light collector including a spacer that includes a top aperture and bottom aperture. The top aperture and bottom are typically co-axial. The spacer provides the separation between the entrance to the device and the light detector to ensure that the incoming light is properly diffused before contacting the light detector, e.g., reducing intensity "hot spots" while allowing for sufficient expansion of the diffused light to ensure contact of the light over the active area of the light detector.

In some cases, the spacer may have thickness from about 4 mm to about 20 mm, e.g., from about 4 mm to about 8 mm, from about 5 mm to about 9 mm, from about 6 mm to about 10 mm, from about 7 mm to about 11 mm, from about 8 mm to about 12 mm, from about 9 mm to about 13 mm, from about 10 mm to about 14 mm, from about 11 mm to about 15 mm, from about 12 mm to about 16 mm, from about 13 mm to about 17 mm, from about 14 mm to about 18 mm, from about 15 mm to about 19 mm, or from about 16 mm to about 20 mm, e.g., about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm.

The spacer, and any cross-section thereof, may be of any suitable shape, e.g., cylindrical, ellipsoidal, or polygonal, e.g., square, rectangular, triangular, or n-gon, or irregular, or any combination thereof. The spacer may have a cross-sectional dimension that is constant or variable. For example, the cross-sectional dimension, e.g., the diameter, may increase or decrease by at least 1%, 5%, 10%, 20%, 30%, 40%, 50%, 60%, 70%, 80%, 90%, or 100%, or at most 1%, 5%, 10%, 20%, 30%, 40%, 50%, 60%, 70%, 80%, 90%, or 100%. In some cases, the cross-section of the spacer may be the same shape along the thickness of the spacer, e.g., a cylinder. Alternatively, the cross-section of the spacer may a combination of one or more shapes along the thickness of the spacer, e.g., a spacer may have a circular cross section at the top aperture and a rectangular cross section at the bottom aperture. For example, the spacer may have a cylindrical cross-section, where the diameter is constant from the top aperture to the bottom aperture. As another example, the spacer may have a truncated conical cross-section, with the diameter increasing from the top aperture to the bottom aperture or decreasing from the top aperture to the bottom aperture.

The spacer may be manufactured from any suitably diffuse reflective material, e.g., polytetrafluoroethylene (e.g., Teflon® or Spectralon® from Labsphere Inc.), polyoxymethylene (e.g., Delrin®), barium sulfate (e.g., 6080 White Reflectance Coating from Labsphere Inc.), polyvinylchloride (PVC), polyamide, e.g., Nylon, co-polyester, poly-lactic acid (PLA), or a Lambertian coating (e.g., Spectraflect® or Duraflect® from Labsphere Inc.). Without wishing to be bound by any particular theory, the chosen material for the spacer reflects light without spectral distortion. Other diffusely reflective materials are known in the art.

Light passing through the top aperture of the spacer may be diffused by a light diffusing layer, e.g., a thin film such as a Lee Filters 452 $\frac{1}{16}^{th}$ white diffusion film, that diffuses light incoming to the device. The bottom aperture of the spacer may include a recess for a light detector, e.g., a photovoltaic detector, e.g., an amorphous silicon photovoltaic detector such as a Panasonic Amorton photovoltaic cell.

Examples of a spacer having a top aperture and bottom aperture including a recess for a light detector are shown in FIGS. 3A-3F. In this configuration, a light diffusing layer may be placed above the top aperture of the spacer. The diffused light contacts the light detector located in the bottom aperture's recess to produce a signal representative of a characteristic of the light.

In some cases, the spacer does not include a detector, e.g., a photovoltaic detector, connected to the bottom aperture. The bottom aperture of the light diffusing element may include a connection to a light conducting conduit, e.g., a waveguide, fiber optic, or liquid light guide. In this configuration, a light detector receives diffused light from the light conducting conduit.

External Shell

In some cases, the spacer is contained within an external shell, e.g., two or more portions such as a top portion and a bottom portion that mate together to enclose the spacer. The top portion includes an entrance to allow light to enter the spacer. The external shell may contain, in addition to the spacer, a power supply, e.g., a battery such as a rechargeable battery, a microcontroller, and any electrical connections that facilitate various functions of the device, e.g., data collection, data transfer, and/or power transmission. The exterior shape of the external shell may substantially correspond to the shape of the spacer. Alternatively, the shape of the external shell may be of any suitable shape that is dimensioned to contain all components, e.g., the spacer and any electrical components.

The entrance of the top of the external shell may be of any suitable shape to allow light to enter the device. For example, the entrance may be circular, ellipsoidal, or polygonal, e.g., square, rectangular, triangular, or n-gon, or irregular. The entrance of the external shell may be positioned to allow light to enter the spacer centered around the central axis of the spacer. In some cases, the entrance includes a resting location, e.g., to rest a light source in a stable, repeatable position. The resting location may be a notch, groove (e.g., V-groove), or other perturbation in the perimeter of the aperture to allow the light source to rest. The resting location may be further configured to align the central axis of the light source with the center of the spacer. In particular embodiments, the entrance of the top portion of the external shell has an irregular shape, e.g., "tear drop" shape. In a non-limiting example, a tear drop shaped entrance provides for stable placement for a light source, such as a dental light curing unit (LCU), where the emitter tip of the LCU rests on the tear drop entrance. In this configuration, the tear drop shape of the entrance allows for the emitter tip of the LCU to be centered over the active element of the light detector, ensuring light that enters the device is diffused and sufficiently expands to cover the active area of the light detector. In another non-limiting example, the shell has an inset feature to guide a light source to the resting location. For example, the inset includes side walls that narrow towards the entrance.

In particular, dental LCU tips come in various sizes, and smaller tips, such as those 7 mm or smaller in diameter, may be susceptible to an inaccurate measurement of the properties of light due to inconsistent placement of the tip into the device. A tear drop shaped entrance to the device assists in aligning a smaller, e.g., less than 7 mm, LCU tip by providing a stable and repeatable location in which to place the tip for measurement. Other irregular shapes may be used to position the light source in the desired location.

In some embodiments, the shell, e.g., adjacent to or at the entrance, e.g., adjacent to or at the resting location, includes a sensor and/or actuator to indicate that the light source is in a desired location, e.g., aligned with the center of the light detector. For example, the shell may include a sensor, e.g., a motion, proximity, or force, e.g., applied force, sensor, that detects the presence of the emitter of the light source and sends a signal, e.g., to initiate data collection or to notify a user that data is ready to be collected. Alternatively or in addition, the shell may include an actuator, such as a mechanical actuator, e.g., a button, that is activated by placement of the light source, e.g., to initiate data collection or to notify a user that data is ready to be collected. The shell may also include other components for use or control of the device, e.g., a power/sleep button, status indicator, and/or a communication port (e.g., for power and/or data).

Figure 4A:
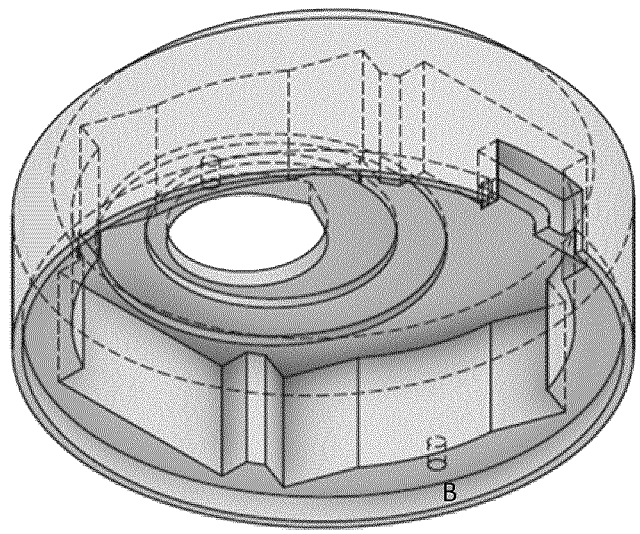
FIG. 4A-4C: Technical drawings of the top and bottom portions of an external shell for a light collecting device of the invention.
Figure 4B:
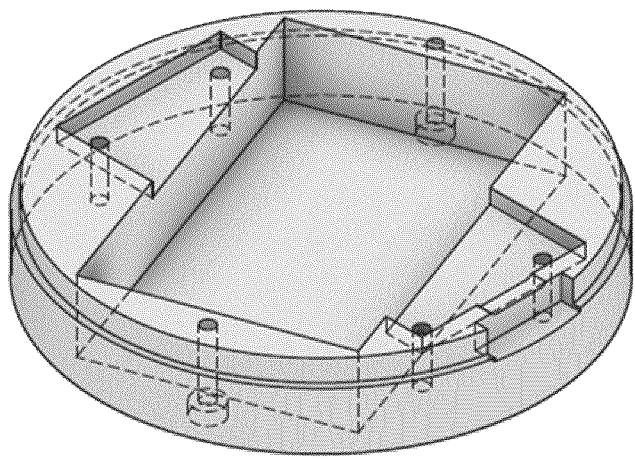
Figure 4C:
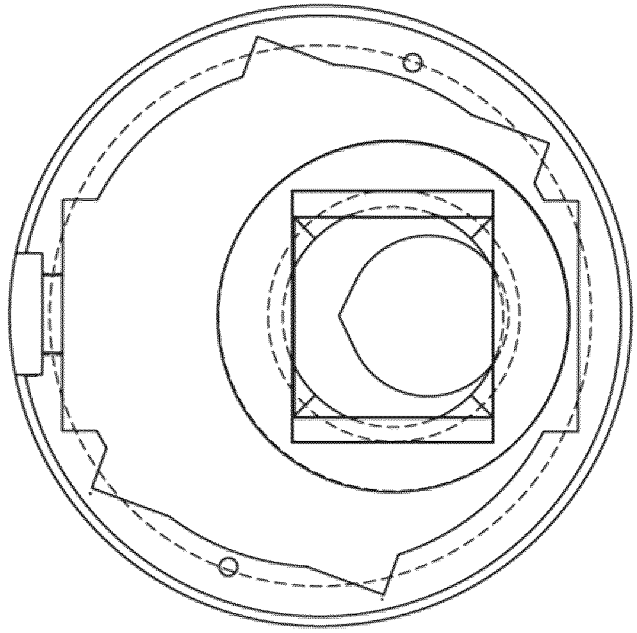

FIGS. 4A-4C show various embodiments of external shell that includes top and bottom portions that include recesses for the spacer (FIG. 4A) and the electrical components (FIG. 4B). FIG. 4C is a line drawing view of the spacer inserted into the top portion of the external shell. The rectangle shown in FIG. 4C is the recess in the bottom aperture of the spacer and in this configuration, the tear drop shaped entrance of the top portion of the external sell is inside of said rectangle, indicating that the light entering the device is directed onto the active area of the light detector installed in the recess. A skilled artisan can appreciate that other configurations of the external shell are possible, including more than two portions or two side portions that mate together.

Figure 5A:
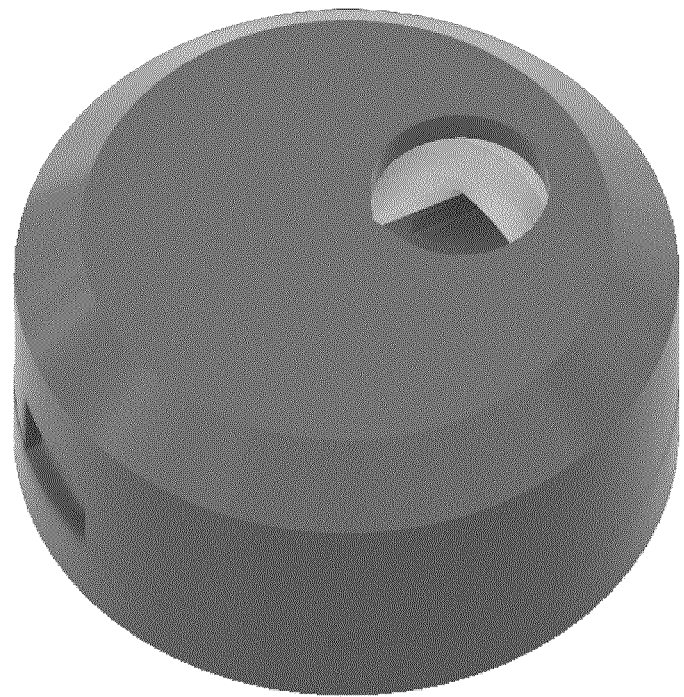
FIGS. 5A-5B: Technical drawings of a device of the invention with a spacer encased in an external shell having an entrance.
Figure 5B:
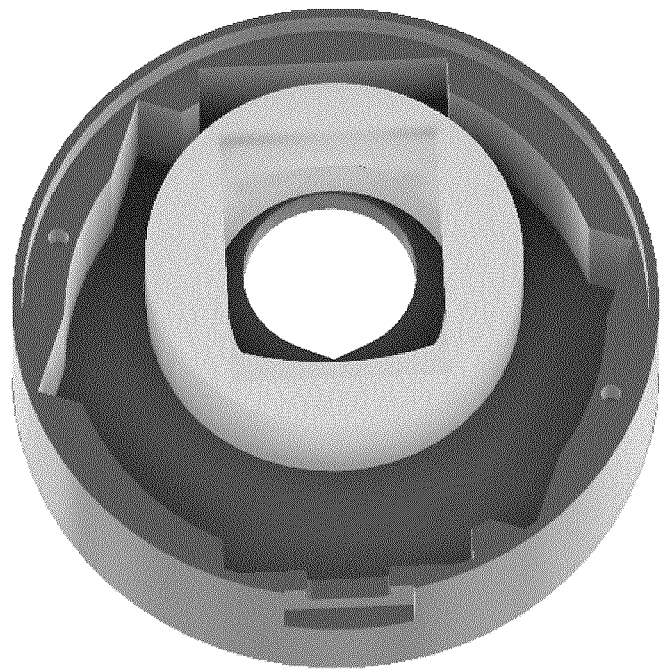

A spacer encased in a cylindrical external shell is shown in FIGS. 5A and 5B. In the embodiment shown in FIGS. 5A-5B, the top portion of the external shell includes a tear drop shaped entrance to the spacer. The internal surface and cavity shape of external shell may vary according to the external shape of the spacer, e.g., it may conform to the exterior shape as shown in FIGS. 5A-5B. Further shown in the embodiment of FIGS. 5A-5B is a small recess configured to accept a data and or power communication cable, e.g., a USB, e.g., a micro USB cable, for providing power to a power source, e.g., a battery, e.g., a rechargeable battery and/or to provide electrical communication with a light detector.

Figure 6A:
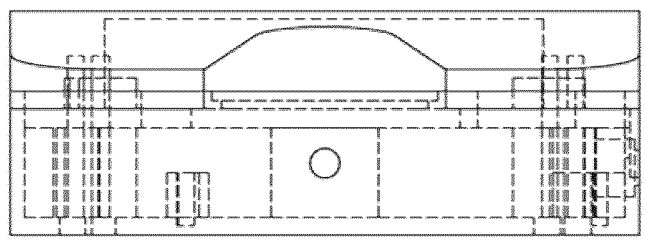
FIGS. 6A-6D: Technical drawings of a device of the invention with an external shell that includes a resting location at the entrance.
Figure 6B:
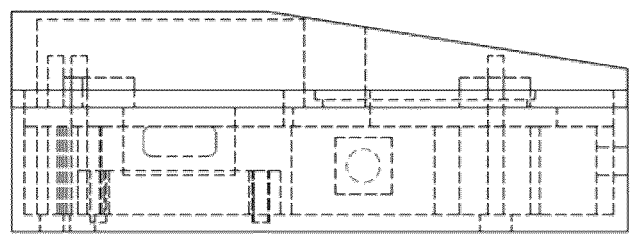
Figure 6C:
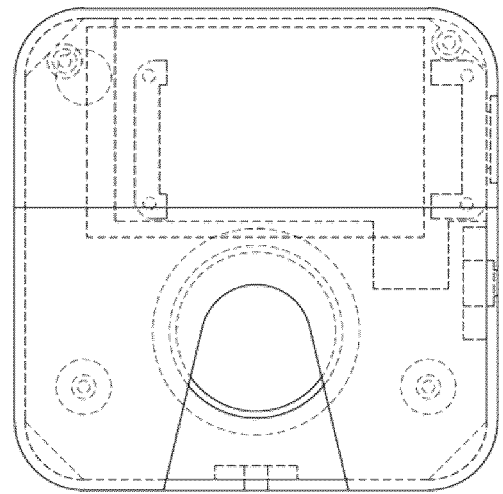
Figure 6D:
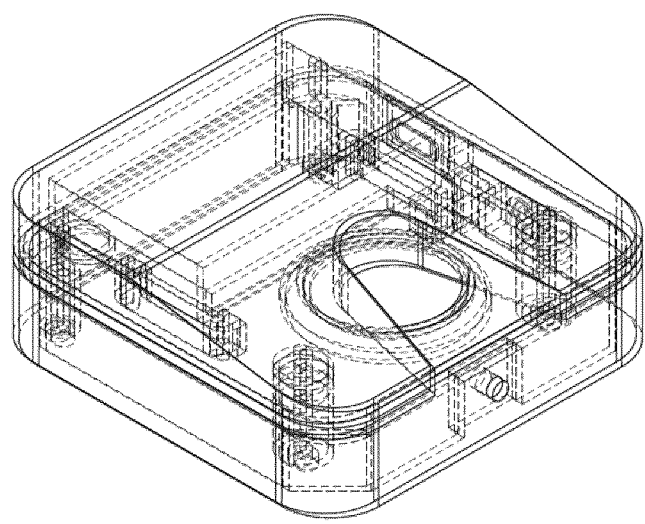
Figure 7:
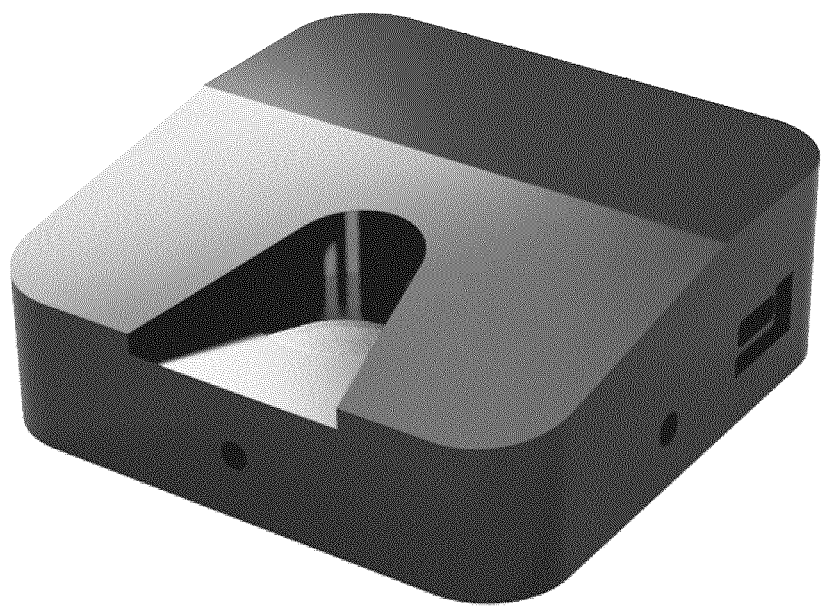
FIG. 7: Technical drawing of a device of the invention with an external shell that includes a resting location at the entrance.

FIGS. 6A-6D show various line drawings of an embodiment of the invention with an external shell having an inset that guides a light source to a resting location in the entrance. FIGS. 6A-6B are front and side views of the external shell showing the resting location. FIG. 6C is a line drawing view of the top of the device. FIG. 6D is a perspective view. FIG. 7 shows the external shell of FIGS. 6A-6D. The embodiment of an external shell shown in FIG. 7 includes a recess on the side configured to accept a data and/or power communication cable, e.g., a USB, e.g., a micro USB cable, for providing power to a power source, e.g., a rechargeable battery, and/or to provide electrical communication with a light detector and a mechanical actuator, e.g., a button, e.g., a power/sleep button. Further shown in the embodiment of an external shell of FIG. 7 is a status indicator, e.g., a visual indicator, e.g., a light, that indicates the status of the device, e.g., on, off, ready to acquire data, or acquiring data.

Figure 3A:
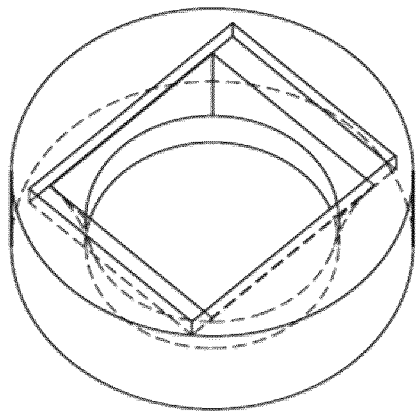
FIGS. 3A-3F: Technical drawings of a spacer for use in a light collecting device showing dimensions in mm.
Figure 3B:
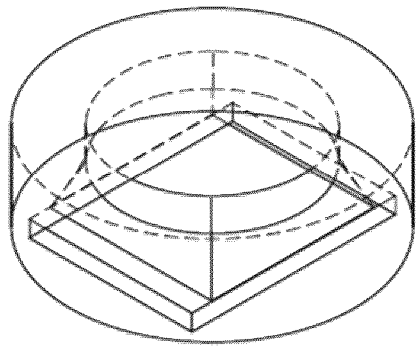
Figure 3C:
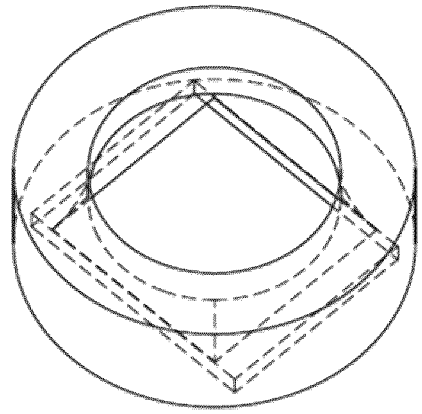
Figure 3D:
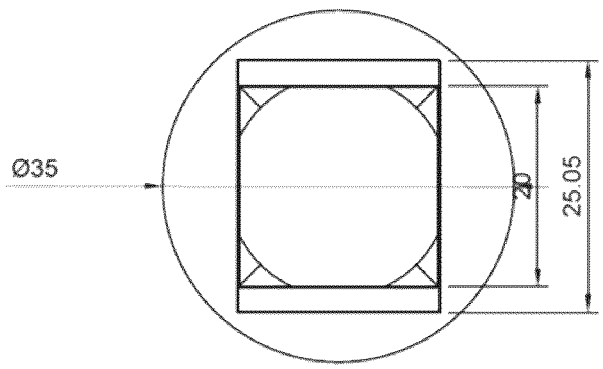
Figure 3E:
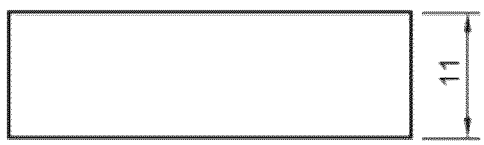
Figure 3F:
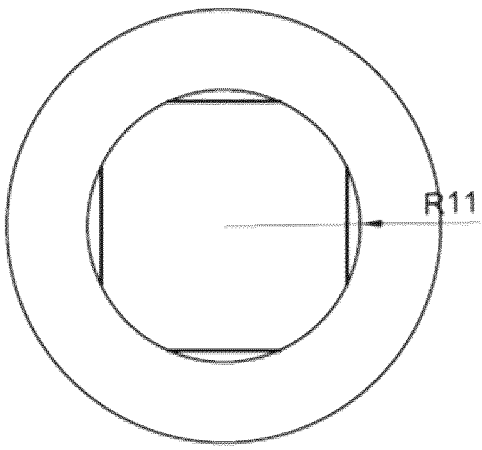

The spacers and light collecting devices shown in FIGS. 3A-3B through FIG. 7 may further include additional components, such as a screen or a filter over an aperture or entrance. For example the top aperture of the spacer may include a screen, and the screen may be sized to cover at least the top aperture of spacer. The surface of a screen, e.g., the material of the surface or a coating applied to the surface, is white, translucent, and Lambertian, e.g., made from or coated with polytetrafluoroethylene (e.g., Teflon® or SpectraIon® from Labsphere Inc.), polyoxymethylene (e.g., Delrin®), barium sulfate (e.g., 6080 White Reflectance Coating from Labsphere Inc.), polyvinylchloride (PVC), polyamide, e.g., Nylon, poly-lactic acid (PLA), or a Lambertian coating (e.g., Spectraflect® or Duraflect® from Labsphere Inc.). In some embodiments, the device may include a filter, e.g., glass (such as alkali-aluminosilicate sheet toughened glass (Gorilla® glass)), neutral density filter, blue band filter, or a filter that filters wavelengths of at least 500 nm. The filter may be located in the top aperture of spacer above or below a screen. In certain embodiments, the filter acts as a physical barrier to protect the screen from damage.

In some cases, a light collecting device, e.g., to be used as part of the system of the invention, contains a light diffusing layer that diffuses incoming light prior to the light contacting a light detector or light conducting conduit. The light diffusing layer may be located on a device component, such as the external shell or the spacer. For example, the light diffusing layer may be located at the entrance of the external shell, where it may be placed above or below the entrance. In this configuration, the light diffusing layer may be directly connected to the material of the external shell, e.g. using a retaining feature or an adhesive. In some cases, another device component, such as a screen or filter, may be used to secure the light diffusing layer to the external shell. Alternatively, the light diffusing layer may be located at the top aperture of the spacer, where it may be held in position using a retaining feature or an adhesive. As a non-limiting example, the light diffusing layer may be placed on top of the top aperture of the spacer and held in position by friction when the spacer and light diffusing layer are placed into an external shell. As another non-limiting example, the light diffusing layer may be incorporated within the spacer. An exemplary light diffusion layer is a Lee Filters 452 $\frac{1}{16}^{th}$ white diffusion film.

Light Detectors

Figure 8:
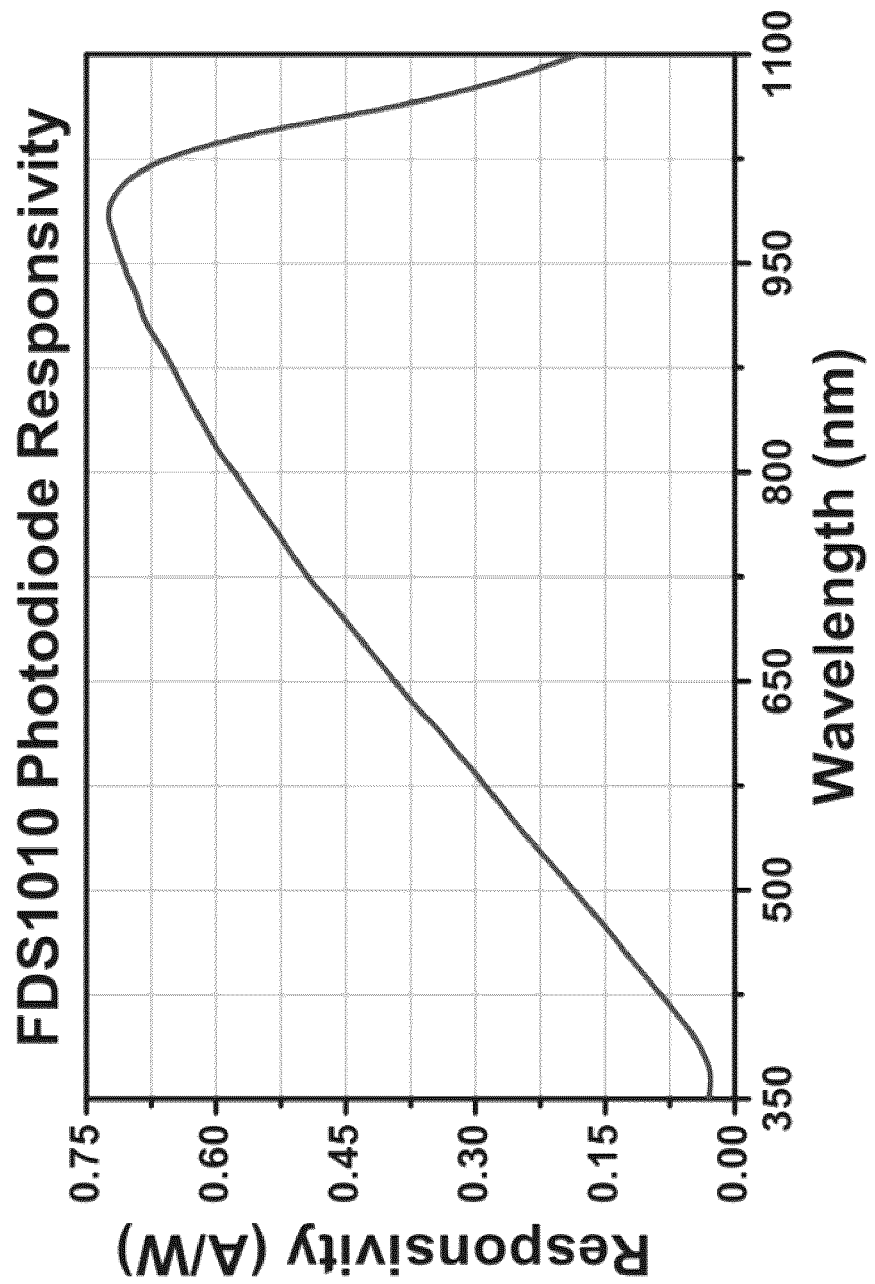
FIG. 8: Responsivity curve of the FDS1010 photodiode configured to act as a light detector in a system of the invention.

A light detector for use in the system of the invention may be any device capable of measuring the intensity of light and encoding the information in an electronic signal, e.g., a photodiode, a photomultiplier tube, a CCD array, a CMOS sensor, thermopile, or a photovoltaic device. In certain embodiments, the detector is non-spectral, i.e., the detector measures the integrated intensity at all wavelengths of light. An exemplary low cost light detector for use in the invention is a photodiode, as it produces a single value for the current (and thus the voltage) resulting from a light source irradiating its active area. Alternatively, a photovoltaic detector may be used, e.g., an amorphous silicon photovoltaic detector such as the Panasonic Amorton photovoltaic cell. Non-spectral light detectors may respond differently to light at different wavelengths, according to an optical characteristic of the source, e.g., a responsivity curve (FIG. 8). The optical characteristic, e.g., responsivity curve, can be used to compensate for this non-uniformity of a light source in the system of the invention. In certain embodiments, spectral light detectors may also be employed, e.g., with a light collector having an outlet port separated from the inner surface by a diffusive material.

Figure 16:
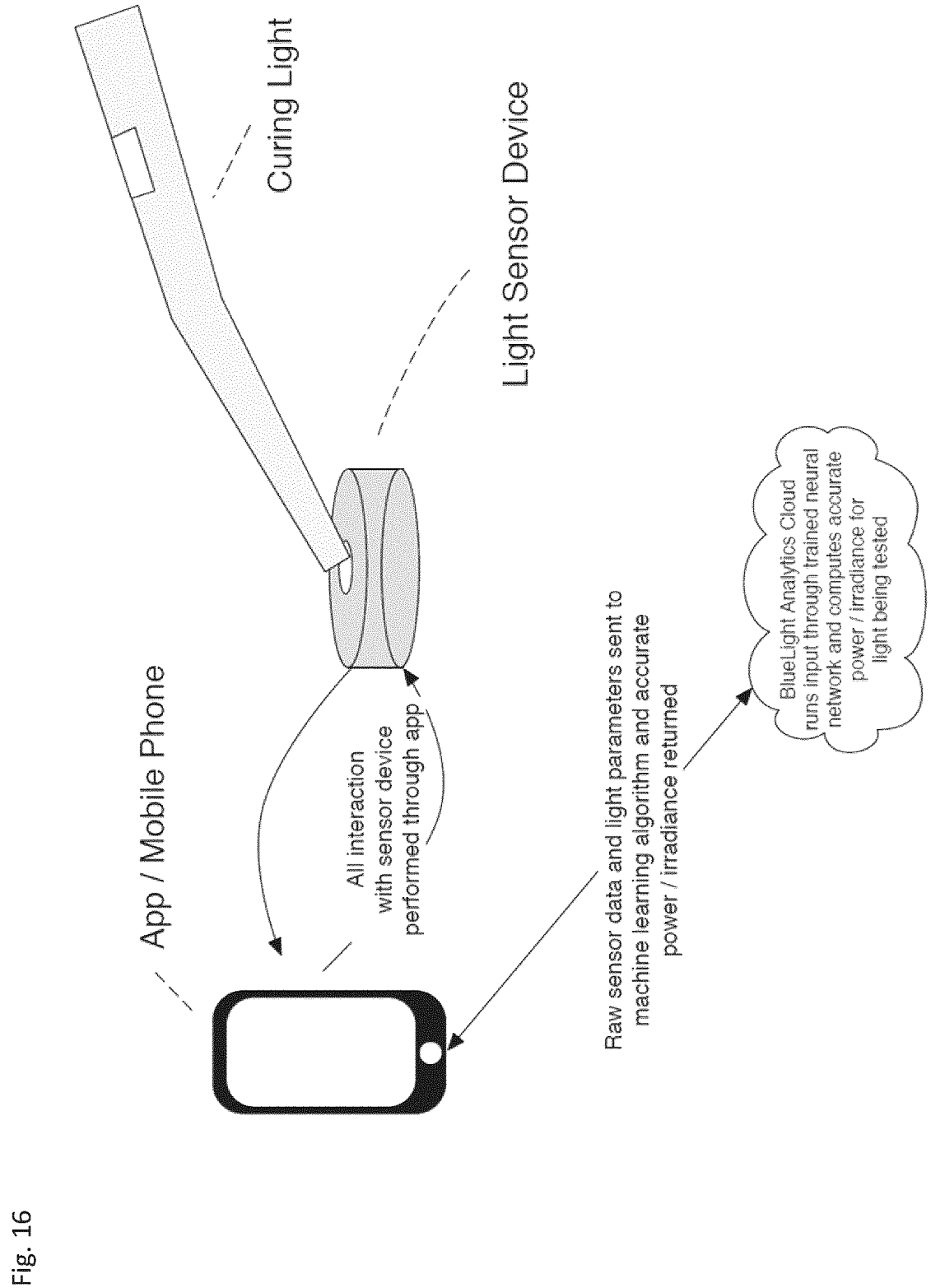
FIG. 16: Scheme describing how a system of the invention may be used to measure an output characteristic, e.g., the output power, of a dental light curing unit (LCU), which is used in determining the length of time.

The detector may interface with a computer programmed to provide the output characteristic, e.g., power, of the light source from the signal produced, which may be the external computer described herein. This detector does not require the use of a spectral detector to produce an output characteristic, e.g., the output power, of a light source, i.e., the light detector is not required to measure intensity as function of wavelength. Typically, the light source will produce light in the range of the IR to UV, e.g., between 100 and 2500 nm, e.g., between 190 and 1000 nm. The light detected may be a subset of the spectrum produced by the light source. For example, various filters may be employed on the light source, the light collector, or both to control the spectrum detected. In certain embodiments, the light detected is in the visible range, e.g., between 360 and 540 nm. An advantage of this detector is that the light collector may communicate remotely, e.g., wirelessly, with the computer, allowing the measurement of an output characteristic, e.g., the output power, to be performed in most locations. This feature is advantageous as the light source may not be portable or easily moved to the location of the computer. A scheme describing how a system of the invention may be used to measure an output characteristic, e.g., the output power, of a device or the invention, is shown in FIG. 16.

Light Device

A light device of the invention includes a light source and a controller operably connected to the light source to control a length of time that the light source emits light. The controller is in data communication with a computer programmed to determine the length of time, which may be continuous or in multiple cycles. The devices, systems, and methods may be generally employed with any light source, including incandescent, laser, LED, halogen, fluorescent, or plasma arc. Typically, the light source will produce light in the range of the IR to UV, e.g., between 100 and 2500 nm, e.g., between 190 and 1100 nm. The light emitted may be a subset of the spectrum produced by the light source. For example, various filters may be employed in the light source to control the spectrum detected. The use of a filter in a light device may also be controlled by the controller. In certain embodiments, the light detected is in the visible range, e.g., between 360 and 540 nm. The light device may also include a plurality of light emitting units, e.g., LEDs, lasers, or light bulbs. The plurality may include light emitting units that have different spectra. The plurality may be individually controllable to alter the spectrum emitted by the light device or to alter the relative power in part of the spectrum emitted.

Figure 15:
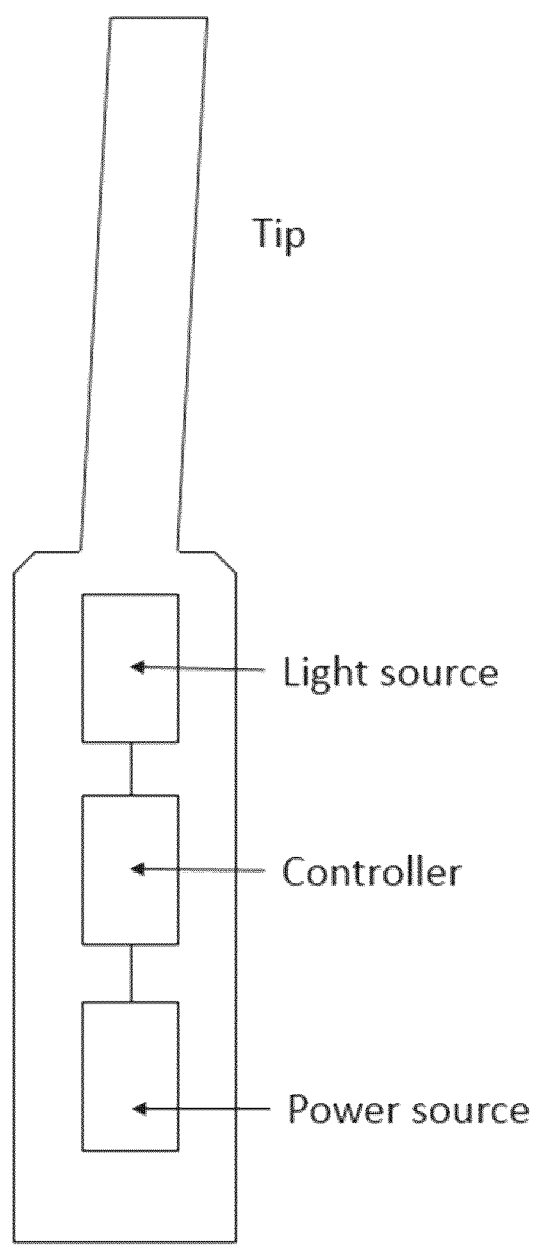
FIG. 15: Schematic drawing of a device according to the invention.

An exemplary device is shown schematically in FIG. 15. In this embodiment, the device includes a tip from which the light is emitted. The device also includes the light source, e.g., LED, the controller, and a power source. For the purposes of the present invention, the term "power source" includes both a generator of the power, e.g., battery, fuel cell, or photovoltaic, or an electrical connection to the power, e.g., a plug or socket to receive a plug. Tips corn in various sizes and shapes, as is known in the art. In certain embodiments, a tip is circular and between 6 mm-14 mm. The device of the invention may also take the approximate physical shape of known light curing units, e.g., Bluephase 20i, 3M DeepCure-L, Coltolux LED, Flashlite Magna, and Smartlite Focus.

The controller is operably connected, e.g., electrically or wirelessly connected, to the light source. By "operably connected" is meant connected in a manner able to control emission from the light source external to the device. Such connection may be directly to the light source or power source, e.g., to allow or interrupt power flow, or to another element in the device, e.g., a shutter, that allows or prevents light from exiting the device. A combination of these types of connection is also envisioned. The controller is also in data communication with a computer programmed to determine the length of time that the light source emits light externally from the device. The data communication can be via a physical connection, such as a USB cable, e.g., a micro USB cable, or similar hardware connection. Alternatively or additionally, the data communication can be via a wireless connection, such as optical, RF, or other wireless connection, e.g., Wi-Fi, near field communication, or Bluetooth®. The controller may also determine the power level of emission, e.g., by altering the voltage or current applied to the light source or by partially closing a shutter or rotating a filter in or out of the light path. Alternatively, the device may have a constant power level or a power level selected by the user, which is taken into account during the determination of the length of time. The controller may allow the length of time to occur continuously, or the controller may allow emission to occur over two or more cycles of light emission. Such cycles may be preferred where continuous emission over the length of time leads to the potential for overheating of the target, which may damage tissue or negatively affect the curing process.

The invention also features systems include a light device of the invention and a computer (or component thereof) and/or a light detector. In particular embodiments, the system includes a device of the invention and a light detector, both of which are capable of being in data communication with a computer.

Figure 17:
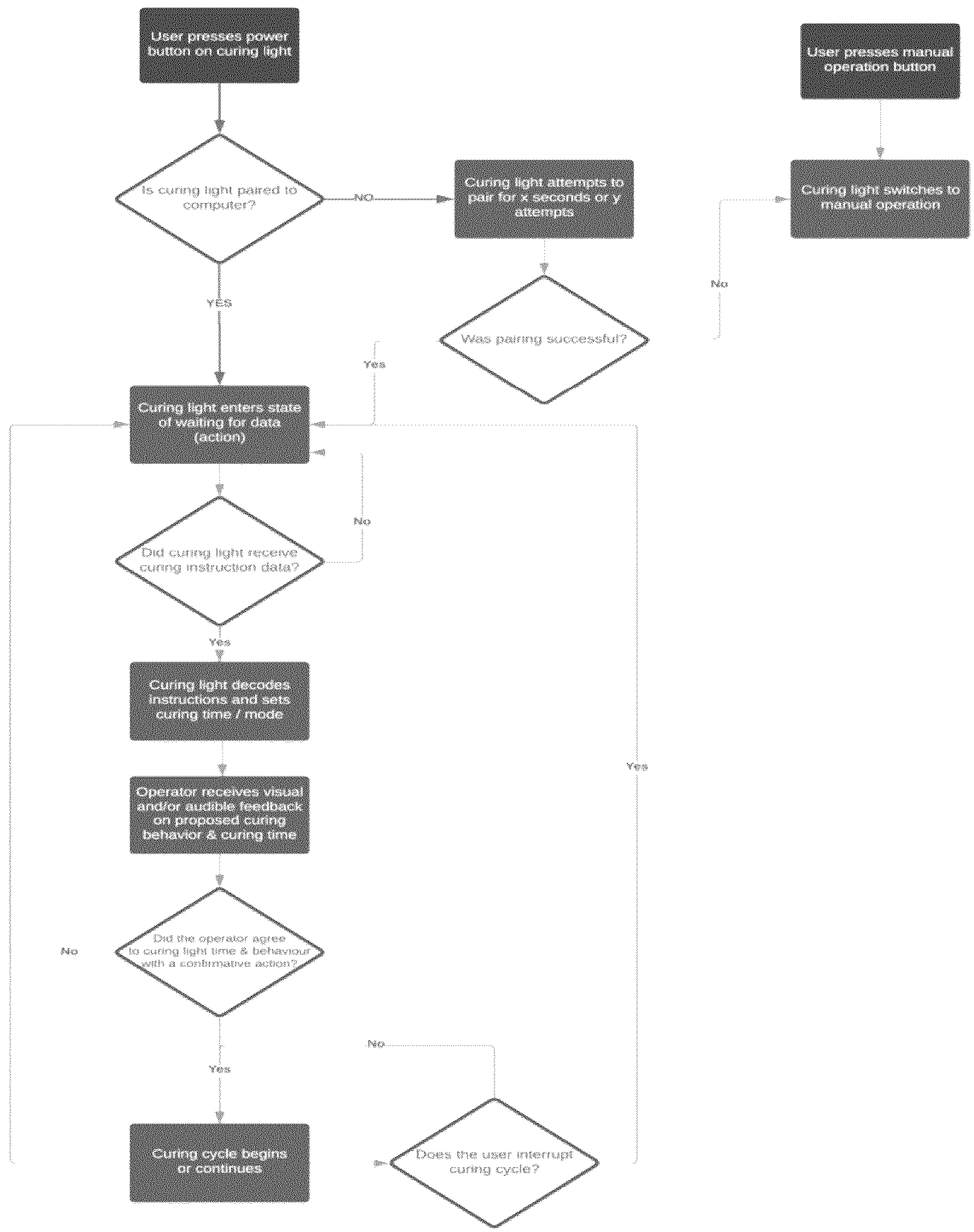
FIG. 17: Flow diagram of how a user would use a system of the invention for measuring an output characteristic, e.g., the output power, of a light source.

FIG. 17 is an exemplary flow diagram of how a user, e.g., dentist or dental assistant, would employ this system of the invention. First, the computer and the detector are paired together over a wireless communications protocol, e.g., Bluetooth® or other wireless transmission protocol, via a mobile device. Once paired, the user can use the mobile device to control all aspects of the measurement. The user can hit "Start" on the mobile device program and then expose the curing light to the light collector for an appropriated length of time. After the data are collected, the integrity of the data is verified, and then the raw data, e.g., normalized voltages from the light detector, are sent wirelessly to a computer programmed, e.g., with a neural network, to calculate the output power of the light source. The data sent to the computer includes the specific light source and light detector used to acquire the data, so the computer uses the correct spectral profile and responsivity curve for its determination. When the determination is complete, the resulting output power of the light source is communicated to the light device and displayed on the mobile device. The user may then review the information and decide whether to initiate illumination, e.g., for resin curing or photodynamic therapy. The user may also pause or stop curing during illumination.

Computer

The data produced by the light collector and light detector may be sent to a computer for processing and provision of the processed data to the user, e.g., by displaying the output characteristic. The computer may be any computer known in the art. Furthermore, the computer may be implemented over several processors or cores or distributed over networks. In one embodiment, a handheld device, e.g., a mobile phone, receives data and transmits it to another processor, which determines the output characteristic or length of time. The output characteristic or length of time is then transmitted back to the mobile device, which in turn transmits it to the controller in a light device of the invention or to the user, e.g., wirelessly, such as optical, RF, Wi-Fi, near field communication, or Bluetooth®. The user interface with the mobile device may be an app, as is known in the art. The computer may also receive the data from the light detector by way of a physical connection, such as a USB cable, e.g., a micro USB cable, or similar hardware connection. The computer is typically external to, i.e., not physically integrated with, the light collector, detector, or light device.

The computer system is programmed to process the data and provide the output characteristic, e.g., power, of the light source to the user or a length of time to a light device. Programming may be via software, hardware, or a combination thereof. Typically, the external computer determines the length of time based on an output characteristic of the device, e.g., output power. The output characteristic may be entered manually into the external computer or measured, either by the external computer or a detector that communicates with the external computer. The computer may be programmed to process the data and provide an output characteristic or a length of time for light emission. Programming may be via software, hardware, or a combination thereof. The data may be processed by a single program. Additionally or alternatively, multiple computer programs may be used in processing the data, and multiple computers may be employed in the processing or provision of the data.

In order for the computer program to be able to provide the output characteristic, e.g., power, of the light source, or length of time it may be programmed to recognize a number of variables about the system. The computer may be programmed with both the spectra of the plurality of light sources it will be used to measure and with an optical characteristic, e.g., the responsivity curve, of the light detector, e.g. a photodiode. The computer may also be programmed for a plurality of light sources and light detectors, with the user selecting the ones being employed. We have found that the spectrum of a light source will be substantially constant independent of the output intensity of the light source due to the use of identical components, e.g., LEDs, in its manufacture. Thus, a light source that has a severely degraded intensity output will still have a nearly identical spectrum as a brand new light source of the same make. This information is programmed into the computer program for the plurality of light sources that will be measured by and have data processed by the program; therefore, the choice of a light source is a user-selectable option before making a measurement. The responsivity curve of a non-spectral light detector relates to the amount of photocurrent produced at every wavelength of light that impinges the detector's active area; the light detector produces a single value for the current corresponding to the integrated response of the light detector at all wavelengths in its range. The computer may be programmed with an optical characteristic, e.g., responsivity curve, of the specific light detector used in the system and also may be user-selectable.

Neural Network

The computer may include a neural network for processing the signal from the light detector. Neural networks are patterned mathematically to acquire, process, and interpret incoming information in a similar way to the human brain, e.g., by taking input information and passing it along to at least one "neuron", further propagating information until terminating at an output. By passing information along to multiple "neurons" the neural network is able to improve the way in which it interprets an input signal, i.e., it learns from previous input signals, thereby improving the accuracy of the end result. The "neurons" are typically organized in layers. Different layers may perform different kinds of transformations on their inputs. Signals travel from the first (input), to the last (output) layer, possibly after traversing the layers multiple times, with each layer performing a mathematical manipulation on the data.

In order for a program such as a neural network to be able to learn from input data and output an appropriate solution to a problem, it first is trained with a set of conditions which represents a correct value or series of values for a problem to be iteratively solved. The training data provides a probabilistic value for the "correct" value of a given problem at each input value. For a neural network of use in the current invention, the training set data may be a combination of the spectra of the plurality of light sources to be measured by the light detector as well as an optical characteristic of the light detector, e.g., the responsivity curve, e.g., power per unit current (W/A) as a function of wavelength. This information may be used to provide probabilistic conditions, e.g. values from 0 to 1, for what the "ideal" power of a light source should be at every wavelength capable of being converted into photocurrent on the light detector.

Figure 9:
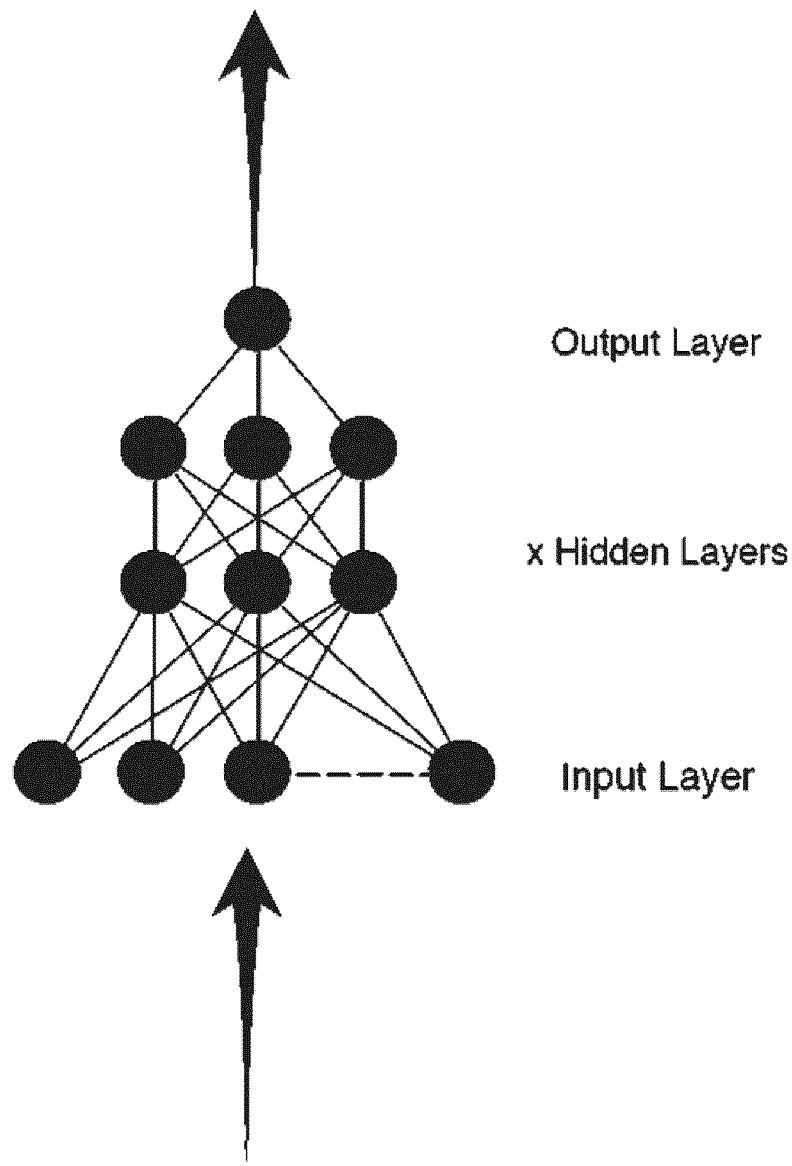
FIG. 9: Diagram of a back-propagation neural network used to measure an output characteristic, e.g., the output power, of a light source using the voltage from a photodiode as input. The circles are nodes, and the lines between nodes are the information being passed from the nodes.

A neural network of a system of the invention may be arranged into three components: the input layer, the hidden layer or layers, and the output layer; this design is known as a back-propagation architecture and a structural diagram of this architecture is showing in FIG. 9. Each of the layers is divided into sub-units called nodes. Within the input, each of the nodes corresponds to a single datum point derived from the output signal of the light detector, e.g., photodiode. The single datum point in each input node is then duplicated and placed into every node in the first of the hidden layers.

The neural network contains at least one hidden layer and may contain others. The number of hidden layers is often linearly correlated with the accuracy and learning ability of the neural network—as the number of hidden layers increases, so too does the accuracy of the resulting output variable, i.e., the output characteristic, e.g., output power of a light source. Each layer consists of a number of individual nodes for receiving data from the previous layer, be it the input layer or another hidden layer within in the neural network. The nodes of the hidden layers contain the probabilistic conditions, e.g., values from 0 to 1, for what the "ideal" power of a light source should be at every wavelength capable of being converted into photocurrent on the light detector. Each node within the hidden layer receives every data point from the previous layer, i.e. the data point from a single node is copied and placed into every node in the next layer of the neural network.

In the hidden layers of the neural network of the invention, the signal from the light detector, e.g., voltage from the photodiode, is multiplied by the wavelength values over the range of the wavelengths from the spectrum from a chosen light source and normalized to produce a series of input values between 0 and 1. These values are then summed together to produce a single value used as input for the transfer function of the neural network, which is a linear or non-linear function used to simulate the learning ability of biological neurons. For neural networks of the invention, this function may be non-linear, e.g., a sigmoidal function, as it has an easily computable derivative. The first derivative is used to calculate the error of the neutral network for improving the learning ability by updating the statistical weights. Alternatively, the transfer function may be rectified. The single value of the summed inputs is directed to the transfer function, e.g., sigmoidal or rectified, returning a single value. This results in a single value for each node in the hidden layer, and each of these datum points is copied and sent as input to every node in the next hidden layer, with every node receiving as input all data from the previous layers' nodes. The process of summing, passing through the transfer function, e.g., sigmoidal or rectified, and passing to the next layer's nodes is repeated for each of the hidden layers of the neural network. Different transfer functions may be used in different layers. For example, the transfer function for one layer may be sigmoidal and may be rectified for another.

The final step in using a neural network of the invention is to pass the data from the final hidden node into the output layer, which includes a final round of summing the data from the nodes of the final hidden layer and passing it through the transfer function, e.g., sigmoidal or rectified, to produce a single output. This output, when un-normalized, returns the power of the light source.

Data Provision

Once the data has been processed by the computer, e.g., programmed with a neural network, the data is provided to the user. The data can be provided by a wired device, such as a computer monitor, or can be a wireless device, e.g., a mobile device such as a cellular telephone or a tablet. An exemplary computer is described in WO 2019/036817. Data may be provided by any suitable means, e.g., visually in a display or audibly from a speaker. Such methods may provide numerical or other data, e.g., a color to signify a certain range of a numerical value. The nature of the provision of data may depend on the output characteristic. For example, data on power, energy, irradiance, or cure time may be provided numerically. Cure time may also be provided in the form of a countdown, which is either numerical or symbolic (e.g., an alarm or other indicator triggers after the cure time has elapsed). Data may also be provided directly to the light source, e.g., to control the length of exposure of the light source.

The output characteristic may be any measure that can be determined from the input data. Examples of output characteristics include output power, output energy, output flux, a calculated spectrum, irradiance, light source age, and calculated exposure time (e.g., time to cure a resin). The output characteristic provided to the user may also be determined in steps. For example, the neural network may provide one output characteristic, e.g., power, which is used by the same or a different computer to determiner another characteristic, e.g., irradiance or cure time, according to known methods.

In addition to length of time, the computer may send information to control the power setting of the device and/or information regarding dividing the length of time over several on/off cycles. The power may also be alternated during the length of time, e.g., alternating between low and high power. Controlling the power and/or on/off cycle may be used to control for excess heat production during illumination.

The computer may also communicate with the controller to alter the spectrum of light emitted, e.g., by turning on or off certain LEDs or altering the relative light output of certain LEDs (e.g., blue or violet) to optimize the cure for the material being used.

Methods of Use

The invention features methods to determine an output characteristic, e.g., the output power, of a light source, e.g., using a computer programmed with a neural network. Typically, the light from the light source is directed into a light collector such that the light is diffused by the light collector's inner surfaces and directed to a light detector. This diffused light impinges on the active area of a light detector, producing a signal representative of an output characteristic, e.g., the output power, of the light source. In some embodiments, the light detector is a non-spectral light detector, e.g., a photodiode. This signal is then sent to the computer to provide an output characteristic, e.g., the output power, of the light source. Once the computer has processed the signal from the light detector, the resulting output characteristic, e.g., output power, of the light source is provided, e.g., displayed, to the user, e.g., on or via a mobile device in substantially real-time. In some embodiments, the computer communicates with the light detector wirelessly, e.g., RF, optical, or other communication standard. Further, the computer may be in wireless communication with the device providing, e.g., displaying, the data. In certain embodiments, the device is a handheld device, e.g., a cellular telephone or a tablet.

The invention also features methods to determine control the length of time of light emission from a light device, e.g., for curing dental resin or photodynamic therapy. Information on an output characteristic, e.g., the output power, of the device is provided to an external computer, e.g., manually or via a light detector. When a light detector is employed, the light may be directed into a light collector such that the light is diffused by the light collector's inner surfaces and directed to a light detector. This diffused light impinges on the active area of a light detector, producing a signal representative of an output characteristic, e.g., the output power, of the light device. In some embodiments, the light detector is non-spectral, e.g., a photodiode. This signal is then sent to the computer to determine the length of time of light emission, which is transmitted back to the light device. In some embodiments, the computer communicates with the light detector and/or light device wirelessly, e.g., Wi-Fi, near field communication, RF, optical, or other communication standard. The computer may also determine a power level of the light device and whether the length of time should be distributed over two or more on/off cycles. For example, the computer may determine that a specific power level or number of cycles is preferable to avoid overheating of a dental resin or surrounding tissue. The length of time may be controlled by on/off switching or the use of filters or apertures to block light from exiting a device.

The length of time will typically be sufficient to cure a specified dental resin in the mouth of a patient or to treat a patient photodynamically. Thus, computer may determine the length of time based not only on the output characteristics of the light device but also the resin employed and/or the type of restoration being undertaken or the type of photodynamic treatment.

The accuracy of the determination of an output characteristic, e.g., the output power, from a light source will depend on the number of individual measurements of an output characteristic, e.g., the output power, of the light source made during a measurement. This is determined by the length of time the active area of the light source is exposed to the light form the light source as well as the sampling frequency of the measurement, e.g., how many data points are collected per unit time. Typical sampling times for measuring an output characteristic, e.g., the output power, of a light source are from about 1 second to about 1000 seconds, e.g., from about 1 second to about 100 seconds, from about 50 seconds to about 200 seconds, from about 150 seconds to about 300 seconds, from about 250 seconds to about 400 seconds, from about 350 seconds to about 500 seconds, from about 450 seconds to about 600 seconds, from about 550 seconds to about 700 seconds, from about 650 seconds to about 800 seconds, from about 750 seconds to about 900 seconds, or about 850 seconds to about 1000 seconds, e.g., about 1 second, about 2 seconds, about 3 seconds, about 4 seconds, about 5 seconds, about 6 seconds, about 7 seconds, about 8 seconds, about 9 seconds, about 10 seconds, about 50 seconds, about 100 seconds, about 150 seconds, about 200 seconds, about 250 seconds, about 300 seconds, about 350 seconds, about 400 seconds, about 450 seconds, about 500 seconds, about 550 seconds, about 600 seconds, about 650 seconds, about 700 seconds, about 750 seconds, about 800 seconds, about 850 seconds, about 900 seconds, about 950 seconds, or about 1000 seconds.

For a method of the invention, the sampling frequency of the light detector varies between about 1 Hertz (Hz) to about 1000 Hz, e.g., from about 1 Hz to about 100 Hz, from about 50 Hz to about 200 Hz, from about 150 Hz to about 300 Hz, from about 250 Hz to about 400 Hz, from about 350 Hz to about 500 Hz, from about 450 Hz to about 600 Hz, from about 550 Hz to about 700 Hz, from about 650 Hz to about 800 Hz, from about 750 Hz to about 900 Hz, or about 850 Hz to about 1000 Hz, e.g., about 1 Hz, about 2 Hz, about 3 Hz, about 4 Hz, about 5 Hz, about 6 Hz, about 7 Hz, about 8 Hz, about 9 Hz, about 10 Hz, about 50 Hz, about 100 Hz, about 150 Hz, about 200 Hz, about 250 Hz, about 300 Hz, about 350 Hz, about 400 Hz, about 450 Hz, about 500 Hz, about 550 Hz, about 600 Hz, about 650 Hz, about 700 Hz, about 750 Hz, about 800 Hz, about 850 Hz, about 900 Hz, about 950 Hz, or about 1000 Hz.

EXAMPLES

Figure 10:
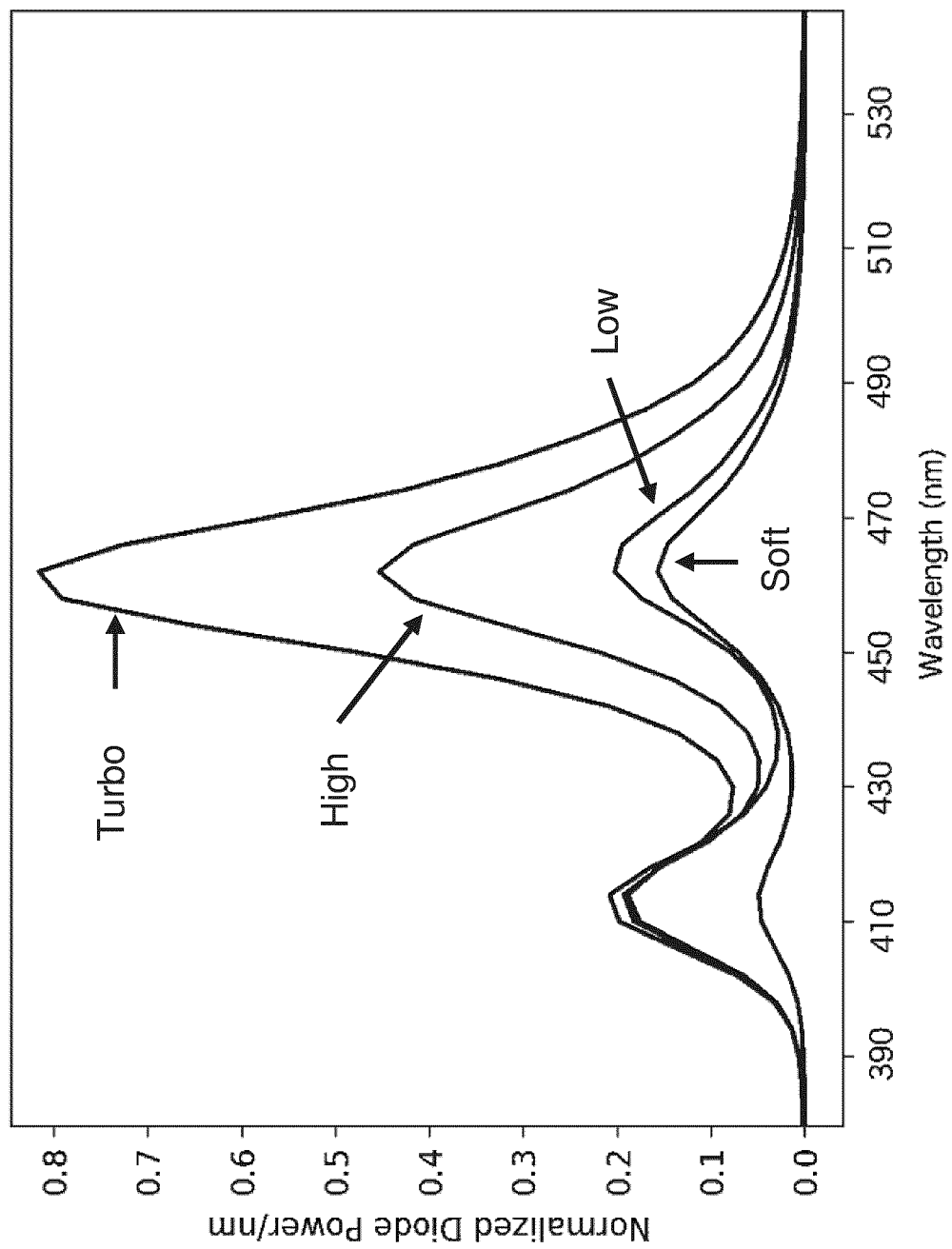
FIG. 10: Spectral profile of the Bluephase 20i dental light curing unit showing the power output in each of the four operating modes, soft mode, low mode, high mode, and turbo mode.

In this example, the system of the invention including a light collector, photodiode, and computer programmed with a neural network was used to measure the power of the Bluephase 20i dental light curing unit (LCU). The Bluephase 20i has four operating modes, each with a different output power of the main light source; in order from lowest power to highest power, the four modes are soft, low, high, and turbo. The spectrum of the Bluephase 20i LCU is shown in FIG. 10. This type of information, in addition to the photodiode responsivity curve shown in FIG. 8, was used as training data to provide probabilistic bounds for the neural network.

When the neural network was fully trained, it takes 1024 input values matching the resolution of the wavelength values produced by the spectrometer. The resulting value is multiplied by the output intensity of the photodiode and subsequently normalized to a value between 0-1. For each input, a single value is produced. When these values are denormalized, the result is the power (in mW) of the light source.

Figure 11A:
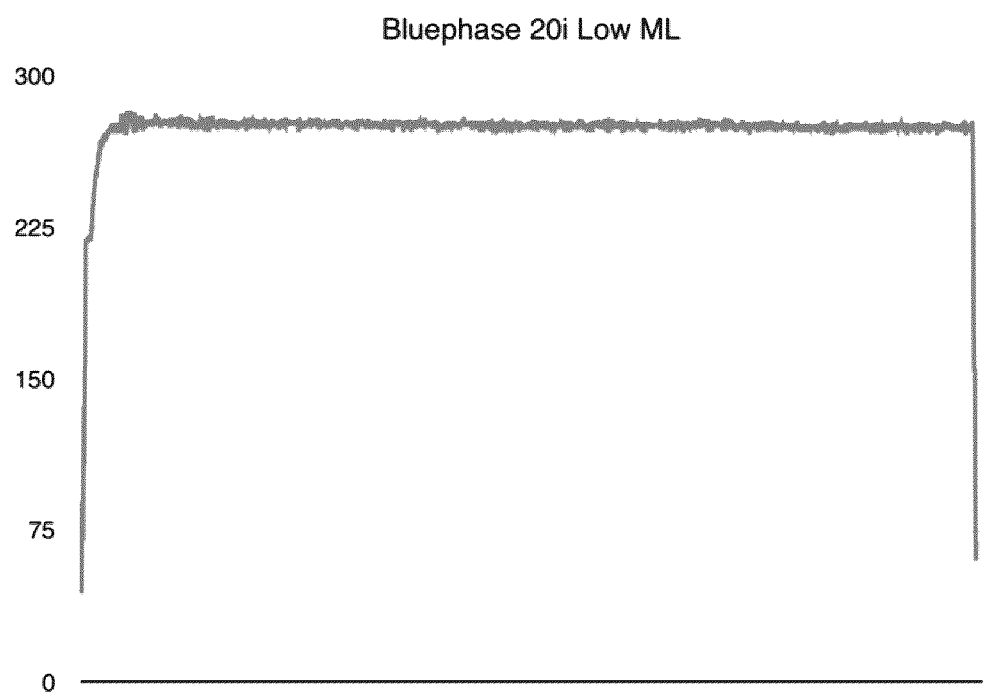
FIG. 11A-11B: Comparison of the output power of the Bluephase 20i dental light curing unit as measured with the photodiode-based neural network system and a conventional spectrometer.
Figure 11B:
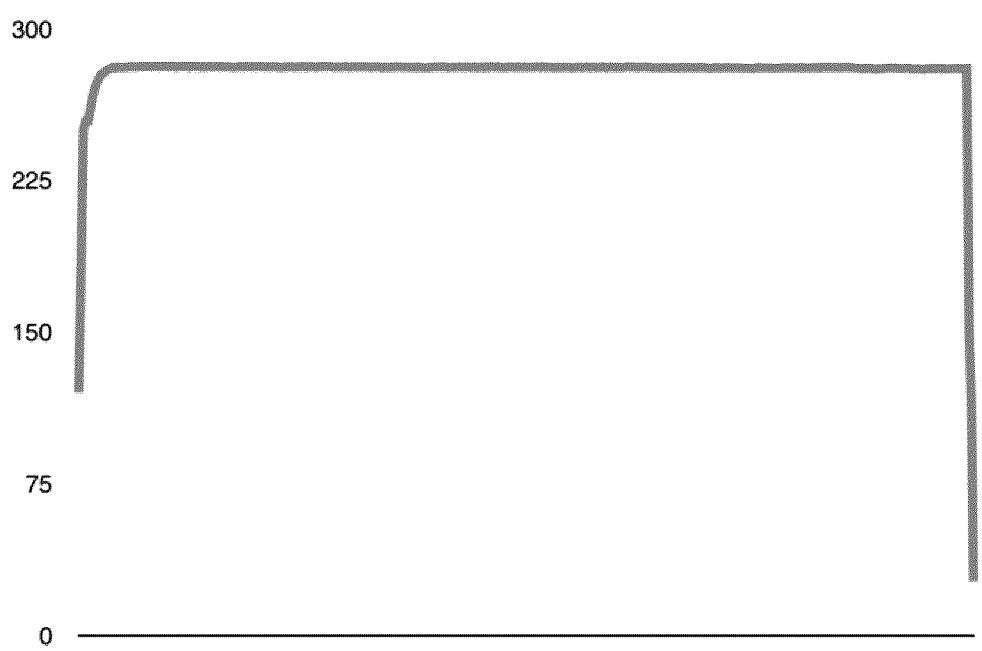

A sampling frequency of 100 readings/second, i.e., 100 Hz, and a cure time of 10 seconds results in an input matrix of [1000,1024] data points that was input into the neural network, resulting in an output matrix of [1000,1]. The results of such output are shown in FIGS. 11A and 11B compared to the same type of measurement using a conventional spectrometer. Using the neural network, the resulting output power measurements come within 5% of the spectrometer.

Figure 12:
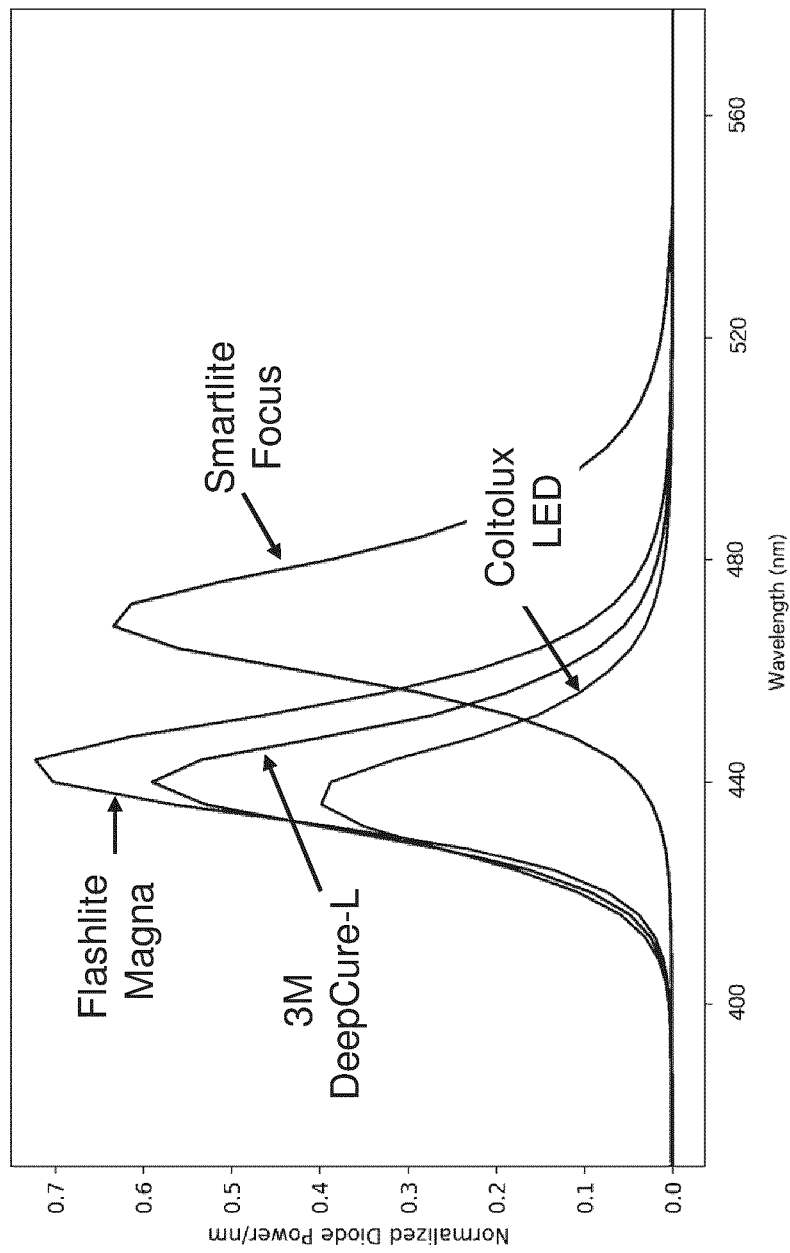
FIG. 12: Spectral profiles of four different dental curing lights as measured with a system of the invention. The lights were 3M DeepCure-L, Coltolux LED, Flashlite Magna, and Smartlite Focus.
Figure 13:
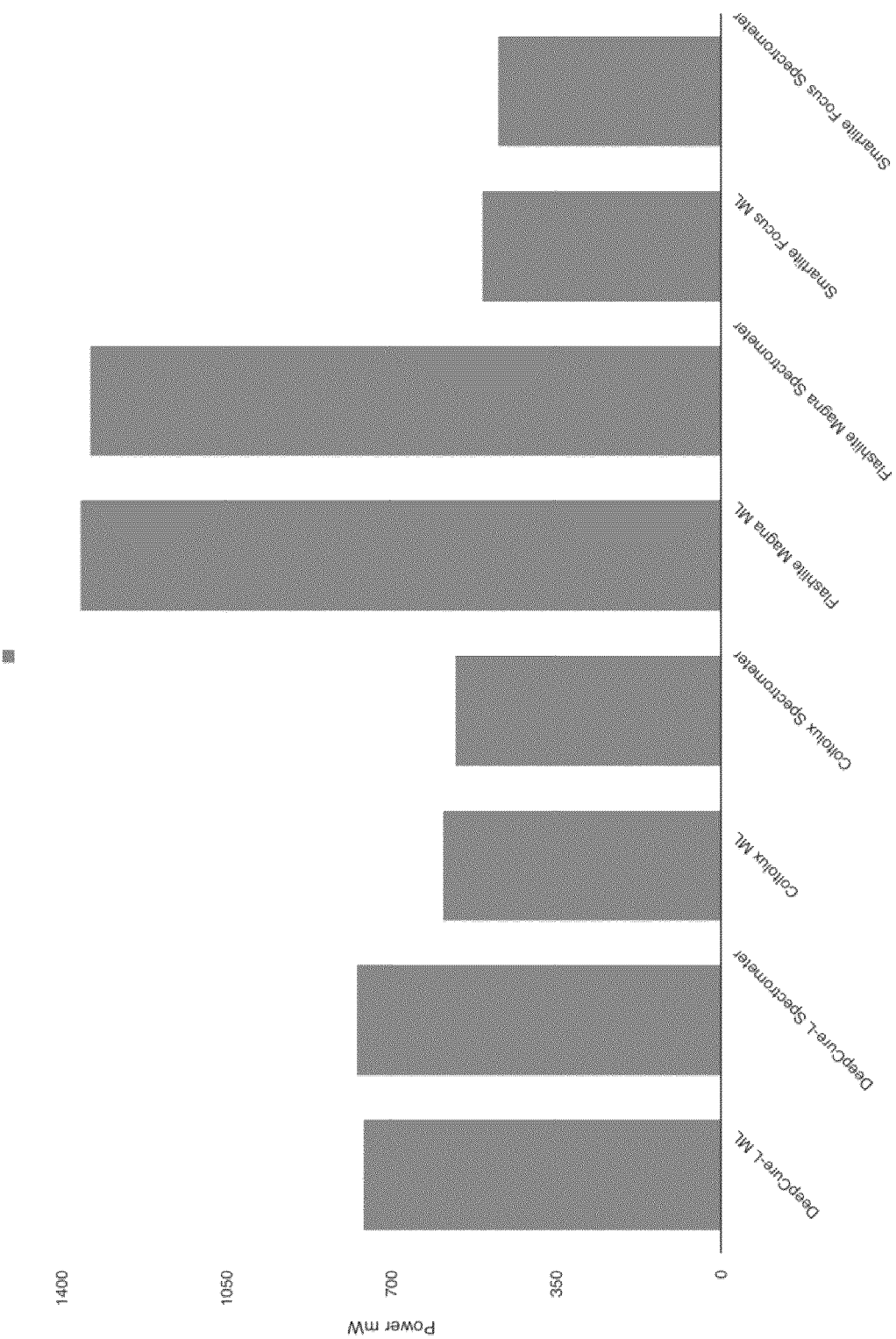
FIG. 13: Comparison of the measured output power for four different curing lights (3M DeepCure-L, Coltolux LED, Flashlite Magna, and Smartlite Focus) using both a system of the invention and a conventional spectrometer.

The spectral profiles of four different curing lights (3M DeepCure-L, Coltolux LED, Flashlite Magna, and Smartlite Focus) were also input into the neural network as training data (FIG. 12). Using the same methodology as used to measure the output power for the Bluephase 20i curing light, the average output power of each of the four curing lights was measured using the photodiode-based neural network system and a conventional spectrometer. The results are shown in FIG. 13, and as before, the average power produced by the photodiode-based neural network system and the spectrometer are again within 5% of each other.

Figure 14:
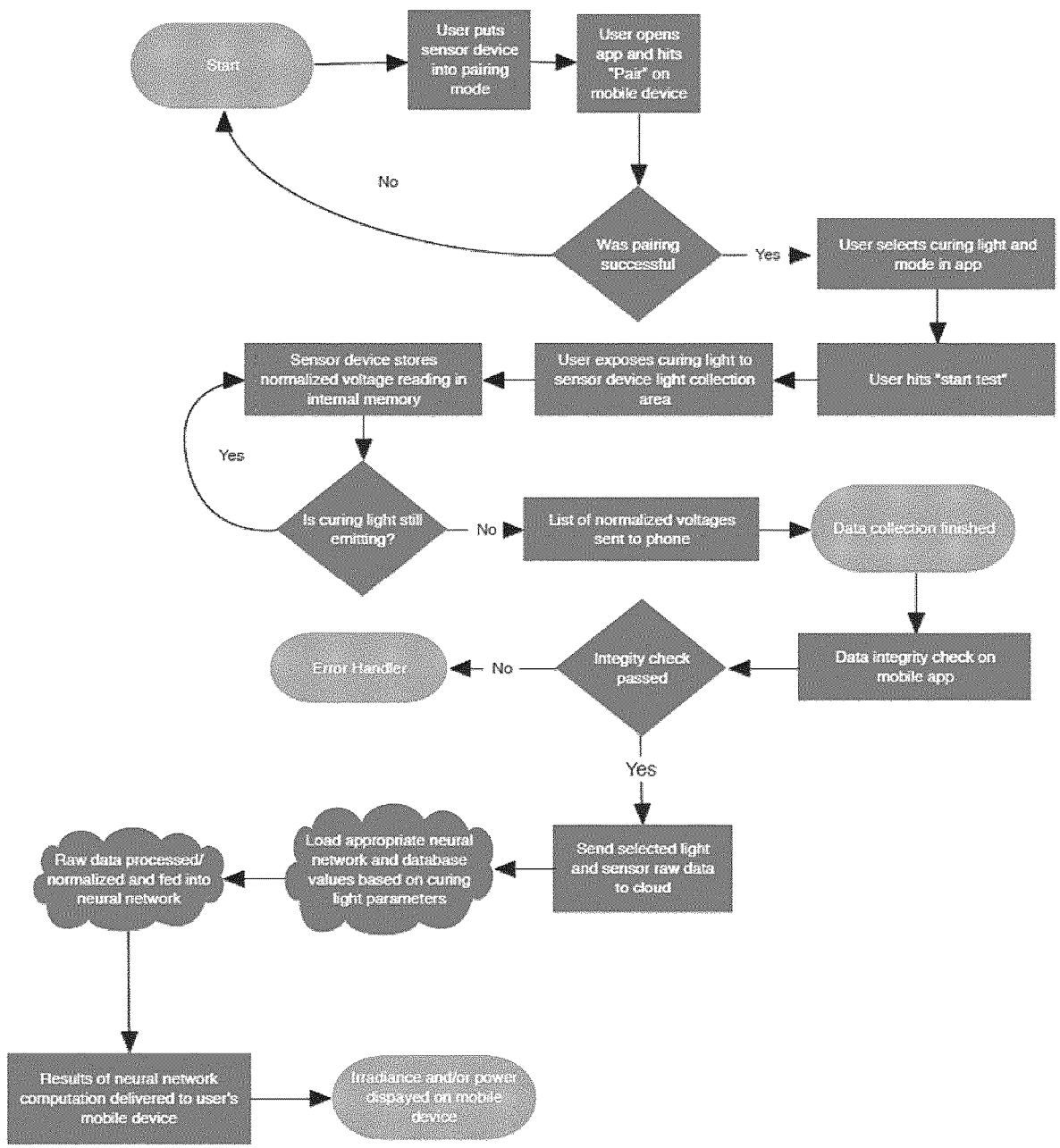
FIG. 14: Flow diagram of how a user would use a system of the invention for measuring an output characteristic, e.g., the output power, of a light source.

The system may be used to measure the power from any light source. An exemplary application for a system of the invention with a light collector, light detector, a computer programmed with a neural network, and a mobile device is for measuring the output power of curing lights used in restoring dental work. FIG. 14 is a flow diagram of how a user, e.g., dentist or dental assistant, would use the system to measure the output power of a curing light. First, the mobile device and the detector are paired together over a wireless communications protocol, e.g., Bluetooth® or other wireless transmission protocol. Once paired, the user can use the mobile device to control all aspects of the measurement. The user can hit "Start" on the mobile device program and then expose the curing light to the light collector for an appropriated length of time. After the data are collected, the integrity of the data is verified, and then the raw data, e.g., normalized voltages from the light detector, are sent wirelessly to a computer programmed with a neural network configured to calculate the output power of the light source. The data sent to the neural network includes the specific light source and light detector used to acquire the data, so the neural network uses the correct spectral profile and responsivity curve for its determination. When the determination is complete, the resulting output power of the light source is displayed on the mobile device.

Other embodiments are in the claims.

What is claimed is:

1. A device comprising:
   a) a light source and
   b) a controller operatively coupled to the light source to control a length of time that the light source emits light externally from the device, wherein the controller is in data communication with an external computer to determine the length of time.

2. The device of claim 1, wherein the computer determines the length of time from a measurement of an output characteristic of the light source and/or wherein the controller is in data communication with the external computer to determine the output power of the light source.

3. A system comprising:
   a) a device of claim 1; and
   b) the external computer.

4. The system of claim 3, further comprising c) a light detector in data communication with the external computer.

5. The system of claim 3, wherein the light detector is non-spectral and/or further comprising a light collector.

6. The system of claim 4, wherein the external computer is further programmed to determine the output power of the device over the length of time.

7. A method of polymerizing a dental resin comprising the steps of:
   a) providing a device of claim 1;
   b) providing an output characteristic of the device to an external computer, wherein the controller is in data communication with an external computer to determine a length of time of light emission based on the output characteristic;
   c) positioning the device adjacent the resin, wherein the device emits light for the length of time, thereby polymerizing the resin.

8. The method of claim 7, wherein the external computer determines the output power of the device over the length of time and/or wherein the length of time is divided over two or more on/off cycles.

9. A method of treating a patient photodynamically comprising the steps of:
   a) providing a device of claim 1;
   b) providing an output characteristic of the device to an external computer, wherein the controller is in data communication with an external computer to determine a length of time of light emission based on the output characteristic;
   c) positioning the device adjacent the patient, wherein the device emits light for the length of time, thereby photodynamically treating the patient.

10. The method of claim 9, wherein the external computer determines the output power of the device over the length of time and/or wherein the length of time is divided over two or more on/off cycles.

* * * * *